(12) United States Patent
Prakash et al.

(10) Patent No.: US 8,536,320 B2
(45) Date of Patent: Sep. 17, 2013

(54) TETRAHYDROPYRAN NUCLEIC ACID ANALOGS

(75) Inventors: Thazha P. Prakash, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 175 days.

(21) Appl. No.: 13/146,188

(22) PCT Filed: Feb. 1, 2010

(86) PCT No.: PCT/US2010/022759
§ 371 (c)(1),
(2), (4) Date: Oct. 10, 2011

(87) PCT Pub. No.: WO2010/090969
PCT Pub. Date: Aug. 12, 2010

(65) Prior Publication Data
US 2012/0022014 A1   Jan. 26, 2012

Related U.S. Application Data

(60) Provisional application No. 61/150,613, filed on Feb. 6, 2009, provisional application No. 61/259,845, filed on Nov. 10, 2009.

(51) Int. Cl.
*C07H 21/04* (2006.01)
(52) U.S. Cl.
USPC ....... 536/24.3; 536/22.1; 536/23.1; 536/24.5; 536/25.5
(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,314,893 A | 5/1994 | Tino et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |

(Continued)

FOREIGN PATENT DOCUMENTS

| | | |
|---|---|---|
| GB | 2366290 | 3/2002 |
| WO | WO 93/25565 | 12/1993 |

(Continued)

OTHER PUBLICATIONS

Abramov et al., "Synthesis of D-Altritol Nucleosides with a 3'-O-tert-butyldimethylsilyl protecting group" Nucleosides, Nucleotides, & Nucleic Acids (2004) 23(1-2):439-455.
Allart et al., "Synthesis of Protected D-Altritol Nucleosides as Building Blocks for Oligonucleotide Synthesis" Tetrahedron (1999) 55:6527-6546.
Allart et al., "D-Altritol Nucleic Acids (ANA): Hybridisation Properties, Stability, and Initial Structural Analysis" Chem. Eur. J. (1999) 5(8):2424-2431.
Altmann et al., "Second Generation of Antisense Oligonucleotides: From Nuclease Resistance to Biological Efficacy in Animals" Chimia (1996) 50:168-176.
Altschul et al., "Basic Local Alignment Search Tool" J. Mol. Med. (1990) 215:403-410.

(Continued)

*Primary Examiner* — Patrick Lewis
(74) *Attorney, Agent, or Firm* — Isis Pharmaceuticals, Inc. Patent Dept.; Casimir Jones, S.C.

(57) ABSTRACT

The present disclosure describes tetrahydropyran nucleoside analogs, oligomeric compounds prepared therefrom and methods of using the oligomeric compounds. More particularly, novel tetrahydropyran nucleoside analogs are provided having at least one chiral substituent that are expected to be useful for enhancing one or more properties of oligomeric compounds such as nuclease resistance and/or binding affinity. In certain embodiments, the oligomeric compounds are expected to hybridize to a portion of a target RNA resulting in loss of normal function of the target RNA.

22 Claims, No Drawings

(56) References Cited

U.S. PATENT DOCUMENTS

| | | |
|---|---|---|
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,607,922 A | 3/1997 | De Clercq et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,763,588 A | 6/1998 | Matteucci et al. |
| 5,792,608 A | 8/1998 | Swaminathan et al. |
| 5,792,747 A | 8/1998 | Schally et al. |
| 5,792,847 A | 8/1998 | Buhr et al. |
| 5,830,653 A | 11/1998 | Froehler et al. |
| 6,005,096 A | 12/1999 | Matteucci et al. |
| 6,426,220 B1 | 7/2002 | Bennett et al. |
| 6,455,507 B1 | 9/2002 | Drach et al. |
| 6,600,032 B1 | 7/2003 | Manoharan et al. |
| 7,276,592 B2 | 10/2007 | Bergmann et al. |
| 7,399,845 B2 | 7/2008 | Seth et al. |
| 7,427,672 B2 | 9/2008 | Imanishi et al. |
| 8,088,904 B2 | 1/2012 | Swayze et al. |
| 2004/0033967 A1 | 2/2004 | Van Aerschot et al. |
| 2004/0033973 A1 | 2/2004 | Manoharan et al. |
| 2008/0038745 A1 | 2/2008 | Bergmann et al. |

FOREIGN PATENT DOCUMENTS

| | | |
|---|---|---|
| WO | WO 94/02499 | 2/1994 |
| WO | WO 94/17093 | 8/1994 |
| WO | WO 99/14226 | 3/1999 |
| WO | WO 01/14400 | 3/2001 |
| WO | WO 02/18406 * | 3/2002 |
| WO | WO 02/36743 | 5/2002 |
| WO | WO 2005/049582 | 6/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Andersen et al., "The synthesis of modified D- and L-Anhydrohexitol nucleosides" Tetrahedron Letters (1996) 37(45):8147-8150.

Atkins et al., "Evaluation of the cellular uptake of hexitol nucleic acids in HeLa cells" Parmazie (2000) 55(8):615-617.

Augustyns et al., "Hybridization specificity, enzymatic activity and biological (Ha-ras) activity of oligonucleotides containing 2,4-dideoxy-B-D-erythro-hexopyranosyl nucleosides" Nucleic Acids Res. (1993) 21(20):4670-4676.

Bass et al., "Double-Stranded RNA as a Template for Gene Silencing" Cell (2000) 101:235-238.

Beaucage, "Advances in the Synthesis of Oligonucleotides by the Phosphoramidite Approach" Tetrahedron (1992) 48(12):2223-2311.

Beaucage, "The Functionalization of Oligonucleotides Via Phosphoramidite Derivatives" Tetrahedron (1993) 49(10):1925-1963.

Beaucage, "The Synthesis of Specific Ribonucleotides and Unrelated Phosphorylated Biomolecules by the Phosphoramidite Method" Tetrahedron (1993) 49(46):10441-10488.

Bihovsky, "Synthesis of C-glucosides by reactions of glucosyl halides with organocuprates" J. Org. Chem. (1988) 53:4026-4031.

Bisacchi et al., "Regioselective Coupling of Tetraalkylammonium Salts of 6-Iodo-2-aminopurine to a Cyclobutyl Triflate: Efficient Preparation of Homochiral BMS-180,194, a Potent Antiviral Carbocyclic Nucleoside" J. Org. Chem. (1995) 60:2902-2905.

Boudou et al., "Base pairing of anhydrohexitol nucleosides with 2,6-diaminopurine, 5-methylcytosine and uracil as base moiety" Nucleic Acids Res. (1999) 27(6):1450-1456.

Brazma et al., "Gene Expression Data Analysis" FEBS Lett. (2000) 480:17-24.

Brown et al., "Activity of Novel Adenine Nucleotide Derivatives as Agonists and Antagonists at Recombinant Rat P2X Receptors" Drug Development Res. (2000) 49:253-259.

Carulli et al., "High Throughput Analysis of Differential Gene Expression" J. Cell. Biochem. Suppl. (1998) 30/31:286-296.

Celis et al., "Gene expression profiling: monitoring transcription and translation products using DNA microarrays and proteomics" FEBS Lett. (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

De Bouvere et al., "Improved Synthesis of Anhydrohexitol Building Blocks for Oligonucleotide Synthesis" Liebigs Ann./Recueil (1997) 1453-1461;1513-1520.

Eckstein, Oligonucleotides and Analogues, A practical Approach, Oxford University Press (2001) New York.
Elbashir et al., "Duplexes of 21-nucleotide RNAs mediate RNA interference in cultured mammalian cells" Nature (2001) 411:494-498.
Elbashir et al., "RNA interference is mediated by 21- and 22-nucleotide RNAs" Genes Dev. (2001) 15:188-200.
Englisch et al., "Chemically Modified Oligonucleotides as Probes and Inhibitors" Angewandte Chemie, International Edition (1991) 30:613.
Fire et al., "Potent and specific genetic interference by double-stranded RNA in *Caenorhabditis elegans*" Nature (1998) 391:806-811.
Flores et al., "Antimalarial antisense activity of hexitol nucleic acids" Parasitol Res. (1999) 85:864-866.
Freier et al., "The ups and downs of nucleic acid duplex stability: structure-stability studies on chemically-modified DNA:RNA duplexes" Nucleic Acids Research (1997) 25(22):4429-4443.
Froeyen et al., "Molecular-Dynamics Studies of Single-Stranded Hexitol, Altritol, Mannitol, and Ribose Nucleic Acids (HNA, MNA, ANA, and RNA, Resp.) and of the Stability of HNA—RNA, ANA—RNA, and MNA—RNA Duplexes" Helvetica Chimica Acta (2000) 83:2153-2182.
Fuchs et al., "Identification of Differentially Expressed Genes by Mutually Subtracted RNA Fingerprinting" Anal. Biochem. (2000) 286:91-98.
Gait et al., Applications of Chemically Synthesized RNA in RNA:Protein Interactions, Ed. Smith (1998) 1-36.
Gallo et al., "2'-C-Methyluridine phosphoramidite: a new building block for the preparation of RNA analogues carrying the 2'-hydroxyl group" Tetrahedron (2001) 57:5707-5713.
Going et al., "Molecular Pathology and Future Developments" Eur. J. Cancer (1999) 35(14):1895-1904.
Greene and Wuts, "Protective Groups in Organic Synthesis" 3rd Edition, John Wiley & Sons, New York (1999).
Hendrix et al., "1',5'-Anhydrohexitol Oligonucleotides: Synthesis, Base Pairing and Recognition by Regular Oligodeoxyribonucleotides and Oligoribonucleotides" Chem. Eur. J. (1997) 3(1):110-120.
Hendrix et al., "1',5'-Anhydrohexitol Oligonucleotides: Hybridisation and Strand Displacement with Oligoribonucleotides, Interaction with Rnase H and HIV Reverse Transcriptase" Chem. Eur. J. (1997) 3(9):1513-1520.
Herdewijn et al., "Targeting RNA with Conformationally Restricted Oligonucleotides" Liebigs Ann. (1996) 1337-1348.
Hossain et al., "Oligonucleotides Composed of 2'-Deoxy-1',5'-anhydro-d-mannitol Nucleosides with a Purine Base Moiety" J. Org. Chem. (1998) 63:1574-1582.
Jungblut et al., "Proteomics in human disease: Cancer, heart and infectious diseases" Electrophoresis (1999) 20:2100-2110.
Jurecic et al., "Long-distance DD-PCR and cDNA microarrays" Curr. Opin. Microbiol. (2000) 3:316-321.
Kang et al., "Inhibition of MDRI gene expression by chimeric HNA antisense oligonucleotides" Nucleic Acids Research (2004) 32(14):4411-4419.
Kozlov et al., "A Highly Enatio-Selective Hexitol Nucleic Acid Template for Nonenzymatic Oligoguanylate Synthesis" J. Am. Chem. Soc. (1999) 121:1108-1109.
Kozlov et al., "Nonenzymatic Synthesis of RNA and DNA Oligomers on Hexitol Nucleic Acid Templates: The Importance of the A Structure" J. Am. Chem. Soc. (1999) 121(12):2653-2656.
Kozlov et al., "Efficienct Transfer of Information from Hexitol Nucleic Acids to RNA during Nonenzymatic Oligomerization" J. Am. Chem. Soc. (1999) 121:5856-5859.
Kozlov et al., "Nonenzymatic Template-Directed Reactions on Altritol Oligomers, Preorganized Analogues of Oligonucleotides" Chem. Eur. J. (2000) 6(1):151-155.
Kroschwitz, The Concise Encyclopedia of Polymer Science and Engineering, Kroschwitz ed., John Wiley & Sons (1990) pp. 858-859.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotechnol. (2000) 80:143-157.
Lescrinier et al., "Solution structure of a HNA-RNA hybrid" Chemistry & Biology (2000) 7:719-731.
Lescrinier et al., "Solution Structure of a Hexitol Nucleic Acid Duplex with Four Consecutive T-T Base Pairs" Helvetica Chimica Acta (2000) 83:1291-1310.
Leumann, "DNA Analogues: From Supramolecular Principles to Biological Properties" Bioorganic & Medicinal Chemistry (2002) 10:841-854.
Madden et al., "Serial analysis of gene expression: from gene discovery to target identification" Drug Discov. Today (2000) 5:415-425.
Montgomery et al., "RNA as a target of double-stranded RNA-mediated genetic interference in *Caenorhabditis elegans*" PNAS (1998) 95:15502-15507.
Nishikura et al., "A Short Primer on RNAi: RNA-Directed RNA Polymerase Acts as a Key Catalyst" Cell (2001) 107:415-416.
Ostrowski et al., "5-Substituted Pyrimidines with a 1,5-Anhydro-2,3-dideoxy-D-arabino-hexitol Moiety at N-1: Synthesis, Antiviral Activity, Conformational Analysis, and Interaction with Viral Thymidine Kinase" J. Med. Chem. (1998) 41:4343-4353.
Perez-Perez et al., "Synthesis and antiviral activity of 2-deoxy-1,5-anhydro-D-mannitol nucleosides containing a pyrimidine base moiety" Bioorg. Med. Chem. Lett. (1996) 6(13):1457-1460.
Pochet et al., "Replicative Capability of Anhydrohexitol Analogues of Nucleotides" Nucleosides & Nucleotides (1999) 18(4&5):1015-1017.
Prashar et al., "READS A Method for Display of 3'-End Fragments of Restriction Enzyme-Digested cDNAs for Analysis of Differential Gene Expression" Methods Enzymol. (1999) 303:258-272.
Sanghvi, Antisense Research and Applications, Crooke and Lebleu ed., CRC Press (1993) Chapter 15, pp. 276-278.
Sanghvi, Antisense Research and Applications, Crooke and Lebleu ed., CRC Press (1993) Chapter 15, pp. 298-302.
Scaringe, "RNA Oligonucleotide Synthesis via 5'-Silyl-2'-Orthoester Chemistry" Methods (2001) 23:206-217.
Sonveaux, "Chapter 1: Protecting Groups in Oligonucleotide Synthesis" Protocols for Oligonucleotide Conjugates, Agrawals Eds, Humana Press, New Jersey (1994) vol. 26, pp. 1-72.
Sutcliffe et al., "TOGA: An automated parsing technology for analyzing expression of nearly all genes" PNAS (2000) 97(5):1976-1981.
Tabara et al., "RNAi in *C. elegans*: Soaking in the Genome Sequence" Science (1998) 282:430-431.
Tijsterman et al., "RNA Helicase MUT-14-Dependent Gene Silencing Triggered in *C. elegans* by Short Antisense RNAs" Science (2002) 295:694-697.
Timmons et al., "Specific interference by ingested dsRNA" Nature (1998) 395:854.
Timmons et al., "Ingestion of bacterially expressed dsRNAs can produce specific and potent genetic interference in *Caenorhabditis elegans*" Gene (2001) 263:103-112.
To, "Identification of Differential Gene Expression by High Throughput Analysis" Comb. Chem. High Throughput Screen. (2000) 3:235-241.
Tuschl et al., "Targeted mRNA degradation by double-stranded RNA in vitro" Genes Dev. (1999) 13:3191-3197.
Van Aerschot et al., "1,5-Anhydrohexitol Nucleic Acids, a New Promising Antisense Construct" Agnew. Chem. Int. Ed. Engl. (1995) 34(12):1338-1339.
Van Aerschot et al., "Increased RNA affinity of HNA analogues by introducing alkoxy substituents at the C-1 or C-3 position" Nucleosides, Nucleotides & Nucleic Acids (2001) 20(4-7):781-784.
Vandermeeren et al., "Biological Activity of Hexitol Nucleic Acids Targeted at Ha-ras and Intracellular Adhesion Molecule-1 mRNA" (2000) 59:655-663.
Vastmans et al., "Recognition of 1,5-Anhydrohexitol Adenine Triphosphate by a DNA Polymerase" Collection Symposium Series (1999) 2:156-160.
Verheggan et al., "Synthesis and Antiherpes Virus Activity of 1,5-Anhydrohexitol Nucleosides" J. Med. Chem. (1993) 36:2033-2040.

Verheggan et al., "Synthesis, Biological Evaluation, and Structure Analysis of a Series of New 1,5-Anhydrohexitol Nucleosides" J. Med. Chem. (1995) 38:826-835.

Verheggan et al., "Synthesis of 1,5-Anhydrohexitol Nucleosides as Mimics of AZT, D4T and DDC+" Nucleosides & Nucleotides (1996) 15(1-3):325-335.

Wang et al., "Cyclohexene Nucleic Acids (CeNA): Serum Stable Oligonucleotides that Activate Rnase H and Increase Duplex Stability with Complementary RNA" J. Am. Chem. (2000) 122:8595-8602.

Wouters et al., "5-Substituted Pyrimidine 1,5-Anhydrohexitols: Conformational Analysis and Interaction with Viral Thymidine Kinase" Bioorganic & Medicinal Chemistry Letters (1999) 9:1563-1566.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotide Phosphate through Incorporation of Modified 2',4'-Carbocyclic-LNAs and -ENAs Leads to Significant Modulation of Antisense Properties" J. Org. Chem. (2009) 74:118-134.

International Search Report for Application No. PCT/US2008/073379 dated Feb. 20, 2009.

International Search Report for Application No. PCT/US2010/022759 dayed Jun. 4, 2010.

* cited by examiner

SEQUENCE LISTING

<160> NUMBER OF SEQ ID NOS: 7

<210> SEQ ID NO 1
<211> LENGTH: 3160
<212> TYPE: DNA
<213> ORGANISM: H. sapeins

<400> SEQUENCE: 1

```
cctcccctcg cccggcgcgg tcccgtccgc ctctcgctcg cctcccgcct ccccctcggtc    60 ttccgaggcg cccgggctcc cggcgcggcg gcggaggggg cgggcaggcc ggcgggcggt   120
gatgtggcag gactctttat gcgctgcggc aggatacgcg ctcggcgctg ggacgcgact   180
gcgctcagtt ctctcctctc ggaagctgca gccatgatgg aagtttgaga gttgagccgc   240
tgtgaggcga ggcggggctc aggcgaggga gatgagagac ggcggcggcc gcggcccgga   300
gcccctctca gcgcctgtga gcagccgcgg gggcagcgcc ctcggggagc cggccggcct   360
```

-continued

```
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cggcacctcc cgctcctgga gcggggggga gaagcggcgg    540
cggcggcggc cgcggcggct gcagctccag ggaggggggtc tgagtcgcct gtcaccattt    600
ccagggctgg gaacgccgga gagttggtct ctcccttct actgcctcca acacggcggc     660
ggcggcggcg gcacatccag ggacccgggc cggttttaaa cctcccgtcc gccgccgccg    720
caccccccgt ggcccgggct ccggaggccg ccggcggagg cagccgttcg gaggattatt    780
cgtcttctcc ccattccgct gccgccgctg ccaggcctct ggctgctgag gagaagcagg    840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt tcttcagcc    1020 acaggctccc agacatgaca gccatcatca aagagatcgt tagcagaaac aaaaggagat   1080
atcaagagga tggattcgac ttagacttga cctatattta tccaaacatt attgctatgg   1140
gatttcctgc agaaagactt gaaggcgtat acaggaacaa tattgatgat gtagtaaggt   1200
ttttggattc aaagcataaa aaccattaca agatatacaa tctttgtgct gaaagacatt   1260 atgcaccgc caaatttaat tgcagagttg cacaatatcc ttttgaagac cataacccac    1320
cacagctaga acttatcaaa ccctttgtg aagatcttga ccaatggcta agtgaagatg    1380
acaatcatgt tgcagcaatt cactgtaaag ctggaaaggg acgaactggt gtaatgatat    1440
gtgcatattt attcatcgg ggcaaatttt taaaggcaca agaggcccta gatttctatg     1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt tttttatca agaggataa aacaccatga     2280 aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccctt tttgtgtcaa aaggacattt aaaattcaat taggattaat aaagatggca    2520
ctttcccgtt ttattccagt tttataaaaa gtggagacag actgatgtgt atacgtagga    2580 atttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
```

```
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                            26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                             25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                        30

<210> SEQ ID NO 5
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 5
gcgttttttg ct                                                           12

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 6
cttagcactg gcct                                                         14

<210> SEQ ID NO 7
<211> LENGTH: 14
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: bases at these positions are RNA

<400> SEQUENCE: 7
cutagcactg gccu                                                      14
```

TETRAHYDROPYRAN NUCLEIC ACID ANALOGS

CROSS REFERENCED TO RELATED APPLICATIONS

This application is a U.S. National Phase filing under 35 U.S.C. 371 claiming priority to International Ser. No. PCT/US2010/022759 filed Sep. 23, 2009, which is the non-provisional application of and claims priority under 35 USC 119(e) to U.S. Provisional Ser. No. 61/150,613, filed Feb. 6, 2009 and to U. S. Provisional Ser. No. 61/259,845, filed Nov. 10, 2009, each of which is incorporated herein by reference in its entirety.

FIELD OF THE INVENTION

Provided herein are tetrahydropyran nucleoside analogs, oligomeric compounds prepared therefrom and methods of using the oligomeric compounds. More particularly, the tetrahydropyran nucleoside analogs each have a substituted tetrahydropyran ring replacing the naturally occurring pentofuranose ring. In certain embodiments, the oligomeric compounds are expected to hybridize to a portion of a target RNA resulting in loss of normal function of the target RNA.

SEQUENCE LISTING

The present application is being filed along with a Sequence Listing in electronic format. The Sequence Listing is provided as a file entitled CHEM0056USASEQ.txt, created on Jul. 25, 2011 which is 8 Kb in size. The information in the electronic format of the sequence listing is incorporated herein by reference in its entirety.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example affinity and nuclease resistance. One such group of chemically modified nucleosides includes tetrahydropyran nucleoside analogs wherein the furanose ring is replaced with a tetrahydropyran ring.

The synthesis of tetrahydropyran nucleoside analogs has been reported in the literature, see for example: Verheggen et al., *J. Med. Chem.*, 1995, 38, 826-835; Altmann et al., *Chimia*, 1996, 50, 168-176; Herdewijn et al., *Bioorganic & Medicinal Chemistry Letters*, 1996, 6 (13), 1457-1460; Verheggen et al., *Nucleosides & Nucleotides*, 1996, 15(1-3), 325-335; Ostrowski et al., *J. Med. Chem.*, 1998, 41, 4343-4353; Allart et al., *Tetrahedron.*, 1999, 55, 6527-6546; Wouters et al., *Bioorganic & Medicinal Chemistry Letters*, 1999, 9, 1563-1566; Brown, et al., *Drug Development Res.*, 2000, 49, 253-259; published PCT application: WO 93/25565; WO 02/18406; and WO 05/049582; U.S. Pat. Nos. 5,314,893; 5,607,922; and 6,455,507.

Various tetrahydropyran nucleoside analogs have been described as monomers and have also been incorporated into oligomeric compounds (see for example: Published PCT application, WO 93/25565, published Dec. 23, 1993; Augustyns et al. *Nucleic Acids Res.*, 1993, 21(20), 4670-4676; Verheggen et al., *J. Med. Chem.*, 1993, 36, 2033-2040; Van Aerschol et al., *Angew. Chem. Int. Ed. Engl.*, 1995, 34(12), 1338-1339; Anderson et al., *Tetrahedron Letters*, 1996, 37(45), 8147-8150; Herdewijn et al., *Liebigs Ann.*, 1996, 1337-1348; De Bouvere et al., *Liebigs Ann./Recueil*, 1997, 1453-1461; 1513-1520; Hendrix et al., *Chem. Eur. J.*, 1997, 3(1), 110-120; Hendrix et al., *Chem. Eur. J.*, 1997, 3(9), 1513-1520; Hossain et al, *J. Org. Chem.*, 1998, 63, 1574-1582; Allart et al., *Chem. Eur. J.*, 1999, 5(8), 2424-2431; Boudou et al., *Nucleic Acids Res.*, 1999, 27(6), 1450-1456; Kozlov et al., *J. Am. Chem. Soc.*, 1999, 121, 1108-1109; Kozlov et al., *J. Am. Chem. Soc.*, 1999, 121, 2653-2656; Kozlov et al., *J. Am. Chem. Soc.*, 1999, 121, 5856-5859; Pochet et al., *Nucleosides & Nucleotides*, 1999, 18 (4&5), 1015-1017; Vastmans et al., *Collection Symposium Series*, 1999, 2, 156-160; Froeyen et al., *Helvetica Chimica Acta*, 2000, 83, 2153-2182; Kozlov et al., *Chem. Eur. J.*, 2000, 6(1), 151-155; Atkins et al., *Parmazie*, 2000, 55(8), 615-617; Lescrinier et al., *Chemistry & Biology*, 2000, 7, 719-731; Lescrinier et al., *Helvetica Chimica Acta*, 2000, 83, 1291-1310; Wang et al., *J. Am. Chem.*, 2000, 122, 8595-8602; US Patent Application US 2004/0033967; Published US Patent Application US 2008/0038745; Published and Issued U.S. Pat. No. 7,276,592). DNA analogs have also been reviewed in an article (see: Leumann, J. C, *Bioorganic & Medicinal Chemistry*, 2002, 10, 841-854) which included a general discussion of tetrahydropyran nucleoside analogs (under the name: hexitol nucleic acid family).

Oligomeric compounds having phosphodiester linked 3'-H tetrahydropyran nucleoside analogs (also referred to in the art as HNA—hexitol nucleic acids or 1,5-anhydrohexitol nucleic acids) have been prepared for evaluation in cell assays. The different motifs that have been evaluated are fully modified wherein each monomer is a phosphodiester linked 3'-H tetrahydropyran nucleoside analog and gapped wherein each monomer in the 5' and 3' external regions of the oligomeric compound are each phosphodiester linked 3'-H tetrahydropyran nucleoside analogs and each monomer in the internal region is a phosphorothioate linked deoxyribonucleoside (see: Kang et al., *Nucleic Acids Research*, 2004, 32(14), 4411-4419; Vandermeeren et 42000, 55, 655-663; Flores et al., *Parasitol Res.*, 1999, 85, 864-866; and Hendrix et al., *Chem. Eur. J.* 1997, 3(9), 1513-1520).

Oligomeric compounds having phosphodiester linked 3'-OH tetrahydropyran nucleoside analogs (also referred to in the art as ANA or D-altritol nucleic acids) have been prepared and evaluated both structurally and in vitro (Allart et al., *Chem. Eur. J.*, 1999, 5(8), 2424-2431).

Chemically modified siRNA's having incorporated hexitol nucleotides have been prepared and tested for silencing capacity (see: Published PCT application, WO 06/047842, published May 11, 2006.

Consequently, there remains a long-felt need for agents that specifically regulate gene expression via antisense mechanisms. Disclosed herein are tetrahydropyran nucleoside analogs that are useful in the preparation of antisense compounds for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Tetrahydropyran nucleoside analogs, oligomeric compounds comprising the tetrahydropyran analogs and methods of using the oligomeric compounds are provided herein. The tetrahydropyran nucleoside analogs are expected to impart enhanced properties to oligomeric compounds they are incorporated into.

The variables are defined individually in further detail herein. It is to be understood that the tetrahydropyran nucleoside analogs, oligomer compounds, and methods of use thereof provided herein include all combinations of the embodiments disclosed and variables defined herein.

In certain embodiments, tetrahydropyran nucleoside analogs are provided having formula I:

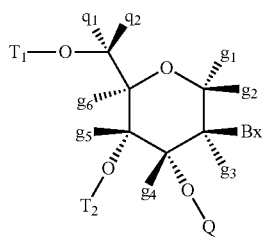

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
Q is $[C(R_1)(R_2)]_n-[(C=O)_m-X]_j-Z$;
each $R_1$ and $R_2$ is, independently, H, $C_1$-$C_6$ alkyl or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $NE_2E_3$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H or $C_1$-$C_6$ alkyl, and L is O, S or $NJ_1$; and
when n is 1 and j is 0 then Z is other than H, and when j is 1, Z is other than halogen.

In certain embodiments, $g_1$, $g_2$, $g_3$, $g_4$, $g_5$, and $g_6$ are each H. In certain embodiments, at least one of $g_1$, $g_2$, $g_3$, $g_4$, $g_5$, and $g_6$ is other than H. In certain embodiments, at least one of $g_1$, $g_2$, $g_3$, $g_4$, $g_5$, and $g_6$ is methyl.

In certain embodiments, $q_1$ and $q_2$ are each H. In certain embodiments, at least one of $q_1$ and $q_2$ is other than H. In certain embodiments, at least one of $q_1$ and $q_2$ is methyl. In certain embodiments, $q_1$ is methyl and $q_2$ is H or $q_2$ is methyl and $q_1$ is H.

In certain embodiments, Bx is uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]primidin-2-one. In certain embodiments, Bx is uracil, 5-methyluracil, thymine, cytosine, 5-methylcytosine, adenine or guanine.

In certain embodiments, each of said hydroxyl protecting groups is, independently, selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX).

In certain embodiments, $T_1$ is selected from acetyl, benzyl, t-butyldimethylsilyl, t-butyl-diphenylsilyl and dimethoxytrityl. In certain embodiments, $T_1$ is 4,4'-dimethoxytrityl.

In certain embodiments, $T_2$ is a reactive phosphorus group. In certain embodiments, $T_2$ is a reactive phosphorus group selected from diisopropylcyanoethoxy phosphoramidite and H-phosphonate.

In certain embodiments, $T_1$ is 4,4'-dimethoxytrityl and $T_2$ is diisopropylcyanoethoxy phosphoramidite.

In certain embodiments, Q is $CH_2F$, $CHF_2$, $CF_3$, $CH_2CH_3$, $CH_2CH_2F$, $CH_2CHF_2$, $CH_2CF_3$, $CH_2-CH=CH_2$, $(CH_2)_2-O-CH_3$, $(CH_2)_3-N(E_2)(E_3)$, $(CH_2)_2-O-N(E_2)(E_3)$, $(CH_2)_2-O-(CH_2)_2-N(E_2)(E_3)$, $CH_2C(=O)-N(E_2)(E_3)$, $CH_2C(=O)-N(E_1)-(CH_2)_2-N(E_2)(E_3)$ or $CH_2-N(E_1)-C(=NJ_1)[N(J_1)(J_2)]$ wherein $E_1$, $E_2$, $E_3$, $J_1$ and $J_2$ are each, independently, H or $C_1$-$C_6$ alkyl. In certain embodiments, Q is $CH_2F$, $CHF_2$, $CF_3$, $CH_2CH_3$, $CH_2CH_2F$, $CH_2CHF_2$, $CH_2CF_3$, $CH_2-CH=CH_2$, $(CH_2)_2-O-CH_3$, $(CH_2)_3-NH_2$, $(CH_2)_2-O-N(CH_3)_2$, $(CH_2)_2-O-(CH_2)_2-N(CH_3)_2$, $CH_2C(=O)N(H)CH_3$ or $CH_2C(=O)-N(H)-(CH_2)_2-N(CH_3)_2$ or $CH_2-N(H)-C(=NH)NH_2$. In certain embodiments, Q is $CH_2F$, $CHF_2$, $CF_3$, $CH_2CH_3$, $CH_2CH_2F$, $CH_2CHF_2$, $CH_2CF_3$, $CH_2CH_2-O-CH_3$ or $CH_2C(=O)N(H)CH_3$. In certain embodiments, Q is $CH_2CH_2F$, $CH_2CH_2-O-CH_3$ or $CH_2C(=O)N(H)CH_3$.

In certain embodiments, oligomeric compounds are provided comprising at least one tetrahydropyran nucleoside analog of Formula II:

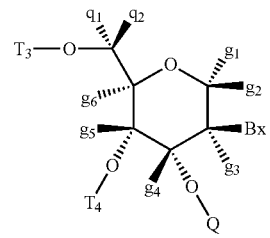

wherein independently for each of said at least one tetrahydropyran nucleoside analog of Formula II:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group or a 5' or 3'-terminal group;
Q is $[C(R_1)(R_2)]_n-[(C=O)_m-X]_j-Z$;

each $R_1$ and $R_2$ is, independently, H, $C_1$-$C_6$ alkyl or halogen;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $NE_2E_3$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

wherein each substituted group comprises one or more optionally protected substituent groups independently selected from halogen, $OJ_1$, $NJ_1J_2$, $SJ_1$, $N_3$, CN, OC(=L)$J_1$, OC(=L)-$NJ_1J_2$ and $NJ_3$C(=L)$NJ_1J_2$, wherein each $J_1$, $J_2$ and $J_3$ is, independently, H or $C_1$-$C_6$ alkyl, and L is O, S or $NJ_1$; and when n is 1 and j is 0 then Z is other than H, and when j is 1, Z is other than halogen.

In certain embodiments, each $g_1$, $g_2$, $g_3$, $g_4$, $g_5$, and $g_6$ is H for each of said at least one tetrahydropyran nucleoside analog of Formula II. In certain embodiments, at least one of $g_1$, $g_2$, $g_3$, $g_4$, $g_5$, and $g_6$ is other than H for each of said at least one tetrahydropyran nucleoside analog of Formula II. In certain embodiments, at least one of $g_1$, $g_2$, $g_3$, $g_4$, $g_5$, and $g_6$ is methyl for each of said at least one tetrahydropyran nucleoside analog of Formula II.

In certain embodiments, each $q_1$ and $q_2$ is H for each of said at least one tetrahydropyran nucleoside analog of Formula II. In certain embodiments, at least one of $q_1$ and $q_2$ is other than H for each of said at least one tetrahydropyran nucleoside analog of Formula II. In certain embodiments, $q_1$ is methyl and $q_2$ is H, or $q_2$ is methyl and $q_1$ is H for each of said at least one tetrahydropyran nucleoside analog of Formula II.

In certain embodiments, Q is $CH_2F$, $CHF_2$, $CF_3$, $CH_2CH_3$, $CH_2CH_2F$, $CH_2CHF_2$, $CH_2CF_3$, $CH_2$—CH=$CH_2$, $(CH_2)_2$—O—$CH_3$, $(CH_2)_3$—N($E_2$)($E_3$), $(CH_2)_2$—O—N($E_2$)($E_3$), $(CH_2)_2$—O—$(CH_2)_2$—N($E_2$)($E_3$), $CH_2$C(=O)N($E_2$)($E_3$), $CH_2$C(=O)—N($E_1$)—$(CH_2)_2$—N($E_2$)($E_3$) or $CH_2$—N($E_1$)—C(=$NJ_1$)[N($J_1$)($J_2$)] wherein $E_1$, $E_2$, $E_3$, $J_1$ and $J_2$ are each, independently, H or $C_1$-$C_6$ alkyl or each of said at least one tetrahydropyran nucleoside analog of Formula II. In certain embodiments, Q is $CH_2F$, $CHF_2$, $CF_3$, $CH_2CH_3$, $CH_2CH_2F$, $CH_2CHF_2$, $CH_2CF_3$, $CH_2$—CH=$CH_2$, $(CH_2)_2$—O—$CH_3$, $(CH_2)_3$—$NH_2$, $(CH_2)_2$—O—N($CH_3$)$_2$, $(CH_2)_2$—O—$(CH_2)_2$—N($CH_3$)$_2$, $CH_2$C(=O)N(H)$CH_3$ or $CH_2$C(=O)—N(H)—$(CH_2)_2$—N($CH_3$)$_2$ or $CH_2$—N(H)—C(=NH)$NH_2$ for each of said at least one tetrahydropyran nucleoside analog of Formula II. In certain embodiments, Q is $CH_2F$, $CHF_2$, $CF_3$, $CH_2CH_3$, $CH_2CH_2F$, $CH_2CHF_2$, $CH_2CF_3$, $CH_2CH_2$—O—$CH_3$ or $CH_2$C(=O)N(H)$CH_3$ for each of said at least one tetrahydropyran nucleoside analog of Formula II. In certain embodiments, Q is $CH_2CH_2F$, $CH_2CH_2$—O—$CH_3$ or $CH_2$C(=O)N(H)$CH_3$ for each of said at least one tetrahydropyran nucleoside analog of Formula II.

In certain embodiments, oligomeric compounds are provided comprising at least one region having at least 2 contiguous tetrahydropyran nucleoside analogs of Formula II. In certain embodiments, each oligomeric compound comprises at least two regions wherein each region independently comprises at least 2 contiguous tetrahydropyran nucleoside analogs of Formula II wherein the two regions are separated by at least one β-D-2'-deoxyribonucleoside.

In certain embodiments, each of the oligomeric compounds provided herein comprise at least two regions wherein each region independently comprises from 1 to about 5 contiguous tetrahydropyran nucleoside analogs of Formula II and wherein the two regions are separated by an internal region comprising at least one monomer subunit wherein each monomer subunit is, independently, a nucleoside or a modified nucleoside. In certain embodiments, gapped oligomeric compounds are provided wherein one of the at least two regions of contiguous tetrahydropyran nucleoside analogs of Formula II is located at the 5'-end and the other of the at least two regions of contiguous tetrahydropyran nucleoside analogs of Formula II is located at the 3'-end and wherein the two regions are separated by an internal region comprising from about 6 to about 18 monomer subunits wherein each monomer subunit is, independently, a nucleoside or a modified nucleoside.

In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to three contiguous tetrahydropyran nucleoside analogs of Formula II, an optional second region of 1 or 2 contiguous tetrahydropyran nucleoside analogs of Formula II and a third region of from 8 to 14 β-D-2'-deoxyribofuranosyl nucleosides wherein said third region is located between said first and said second regions.

In certain embodiments, oligomeric compounds are provided wherein each internucleoside linking group is, independently, a phosphodiester internucleoside linking group or a phosphorothioate internucleoside linking group. In certain embodiments, essentially each internucleoside linking group is a phosphorothioate internucleoside linking group.

In certain embodiments, oligomeric compounds are provided wherein the 5' end of the oligomeric compound comprises a 5'-terminal group or the 3' end of the oligomeric compound comprises a 3'-terminal group.

In certain embodiments, oligomeric compounds are provided comprising from about 8 to about 40 linked monomer subunits. In certain embodiments, oligomeric compounds are provided comprising from about 8 to about 16 linked monomer subunits. In certain embodiments, oligomeric compounds are provided comprising from about 10 to about 14 linked monomer subunits. In certain embodiments, oligomeric compounds are provided comprising from about 14 to about 18 linked monomer subunits.

In certain embodiments, methods of inhibiting gene expression are provided comprising contacting one or more cells, a tissue or an animal with an oligomeric compound of claim 21.

DETAILED DESCRIPTION OF THE INVENTION

Provided herein are novel tetrahydropyran nucleoside analogs, oligomeric compounds that include these tetrahydropyran nucleoside analogs and methods of using the oligomeric compounds. Also included are intermediates and methods for preparing the tetrahydropyran nucleoside analogs and incorporating them into oligomeric compounds. More particularly, tetrahydropyran nucleoside analogs are provided having at least one chiral substituent (—O-Q) attached to the ring carbon furthest away from the ring oxygen atom. In certain embodiments, the tetrahydropyran nucleoside analogs provided herein comprise one or more further chiral groups.

The novel tetrahydropyran nucleoside analogs provided herein are expected to be useful for enhancing one or more properties of the oligomeric compounds they are incorporated into such as for example nuclease resistance and/or hybridization affinity. In certain embodiments, the oligomeric compounds and compositions provided herein that incorporate one or more of the tetrahydropyran nucleoside analogs are expected to hybridize to a portion of a target RNA resulting in loss of normal function of the target RNA. The oligomeric compounds are also expected to be useful as primers and probes in diagnostic applications.

In certain embodiments, tetrahydropyran nucleoside analogs are provided having Formula I:

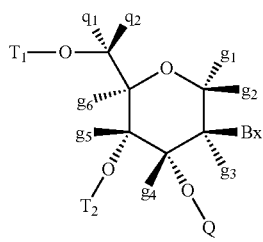

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

Q is $[C(R_1)(R_2)]_n-[(C=O)_m-X]_j-Z$;

each $R_1$ and $R_2$ is, independently, H, $C_1$-$C_6$ alkyl or halogen;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $NE_2E_3$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H or $C_1$-$C_6$ alkyl, and L is O, S or $NJ_1$; and when n is 1 and j is 0 then Z is other than H, and when j is 1, Z is other than halogen.

In certain embodiments, oligomeric compounds are provided herein, wherein each oligomeric compound comprises at least one tetrahydropyran nucleoside analog of Formula II:

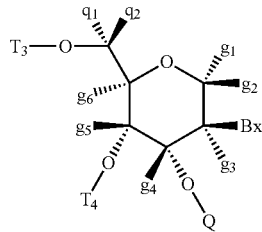

wherein independently for each of said at least one tetrahydropyran nucleoside analog of Formula II:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

Q is $[C(R_1)(R_2)]_n-[(C=O)_m-X]_j-Z$;

each $R_1$ and $R_2$ is, independently, H, $C_1$-$C_6$ alkyl or halogen;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $NE_2E_3$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H or $C_1$-$C_6$ alkyl, and L is O, S or $NJ_1$; and when n is 1 and j is 0 then Z is other than H, and when j is 1, Z is other than halogen.

In certain embodiments, the novel tetrahydropyran nucleoside analogs provided herein are useful for modifying oligomeric compounds at one or more positions. Such modified oligomeric compounds can be described as having a particular motif. Motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as for example a conjugate or reporter group. The positioning of the tetrahydropyran nucleoside analogs provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar groups. The only determinant for the motif of an oligomeric compound is the differences or lack of differences between the sugar groups. As used herein the term "sugar group" as it applies to motifs includes naturally occurring sugars having a furanose ring, sugars having a modified furanose ring and sugar surrogates wherein the furanose ring has been replaced with another ring system such as for example a morpholino or tetrahydropyranyl (also referred to in the art as hexitol) ring system. When each sugar group is the same (DNA, RNA, modified or surrogate) the motif is termed uniformly fully modified. When two or more types of sugar groups are present the motif is defined by the pattern created from the positioning of monomer subunits having one type of sugar group relative to the positioning of monomer subunits having different types of sugar groups within an oligomeric compound.

Illustrative examples of some different types of sugar groups useful in the preparation of oligomeric compounds having motifs include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic modified sugars (such as the 2'-O—CH$_2$-4' or 2'-O—(CH$_2$)$_{2-4}$' bridged ribose derived bicyclic sugars) and sugar surrogates (such as when the ribose ring has been replaced with a morpholino or a tetrahydropyranyl ring system). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar groups, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, one of A and B is a tetrahydropyran nucleoside analog as provided herein.

As used herein the term "uniformly fully modified motif" refers to an oligomeric compound comprising a contiguous sequence of linked monomer subunits that each have the same type of sugar group. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of tetrahydropyran nucleoside analogs as provided herein. In certain embodiments, one or both of the 5' and 3'-ends of the contiguous sequence of tetrahydropyran nucleoside analogs, comprise terminal groups such as one or more unmodified nucleosides.

As used herein the term "hemimer motif" refers to an oligomeric compound comprising a contiguous sequence of monomer subunits that each have the same type of sugar group with a further short contiguous sequence of monomer subunits located at the 5' or the 3' end that have a different type of sugar group. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar groups further comprising a short region (1, 2, 3, 4 or about 5 monomer subunits) having uniform but different sugar groups located on either the 3' or the 5' end of the oligomeric compound.

In certain embodiments, the hemimer motif comprises a contiguous sequence of from about 10 to about 28 monomer subunits having one type of sugar group with from 1 to 5 or from 2 to about 5 monomer subunits having a second type of sugar group located at one of the termini. In certain embodiments, the hemimer is a contiguous sequence of from about 8 to about 20 β-D-2'-deoxyribonucleosides having from 1-12 contiguous tetrahydropyran nucleoside analogs of Formula II located at one of the termini. In certain embodiments, the hemimer is a contiguous sequence of from about 8 to about 20 β-D-2'-deoxyribonucleosides having from 1-5 contiguous tetrahydropyran nucleoside analogs of Formula II located at one of the termini. In certain embodiments, the hemimer is a contiguous sequence of from about 12 to about 18 β-D-2'-deoxyribonucleosides having from 1-3 contiguous tetrahydropyran nucleoside analogs of Formula II located at one of the termini. In certain embodiments, the hemimer is a contiguous sequence of from about 10 to about 14 β-D-2'-deoxyribonucleosides having from 1-3 contiguous tetrahydropyran nucleoside analogs of Formula II located at one of the termini.

As used herein the term "blockmer motif" refers to an oligomeric compound comprising an otherwise contiguous sequence of monomer subunits wherein the sugar groups of each monomer subunit is the same except for an interrupting internal block of contiguous monomer subunits having a different type of sugar group. The heterocyclic base and internucleoside linkage is independently variable at each position of a blocker oligomeric compound. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmer oligomeric compounds are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, each of the two or more regions, independently, have the same or a different type of sugar group. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous tetrahydropyran nucleoside analogs of Formula II each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same. In certain embodiments, each monomer subunit within a particular region has the same sugar group. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising tetrahydropyran nucleoside analogs of Formula II. In certain embodiments, the gapped oligomeric compounds comprise an internal region of β-D-2'-deoxyribonucleosides with both of the external regions comprising tetrahydropyran nucleoside analogs of Formula II. In certain embodiments, gapped oligomeric compounds are provided herein wherein all of the monomer subunits comprise non-naturally occurring sugar groups.

In certain embodiments, gapped oligomeric compounds are provided comprising one or two tetrahydropyran nucleoside analogs of Formula II at the 5'-end, two or three tetrahydropyran nucleoside analogs of Formula II at the 3'-end and an internal region of from 10 to 16 β-D-2'-deoxyribonucleosides. In certain embodiments, gapped oligomeric compounds are provided comprising one tetrahydropyran nucleoside analogs of Formula II at the 5'-end, two tetrahydropyran nucleoside analogs at the 3'-end and an internal region of from 10 to 16 β-D-2'-deoxyribonucleosides. In certain embodiments, gapped oligomeric compounds are provided comprising one tetrahydropyran nucleoside analogs of Formula II at the 5'-end, two tetrahydropyran nucleoside analogs of Formula II at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, through a substituent group or through a bifunctional linking moiety.

The term "oxo" refers to the group (=O).

Linking groups or bifunctional linking moieties such as those known in the art are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "5-terminal group" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (a group for enhancing uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time.

Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenyl)-pethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725, 677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[CH(CH$_3$)$_2$]$_2$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^{V}$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-CH$_2$—C(=O)—N(H)-5'), amide-4 (3'-CH$_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein the phrase "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

The tetrahydropyran nucleoside analogs provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation replacement of the heterocyclic base moiety with a mimetic thereof such as a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar group with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base but abasic modified nucleosides are also envisioned. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar group has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribonucleosides, substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar group has a 2'-O—CHR$_a$-4' bridging group, wherein R$_a$ is H, alkyl or substituted alkyl), other modified nucleosides, nucleoside mimetics and nucleosides having sugar surrogates.

The term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and/or increased stability in the presence of nucleases.

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

The terms "heterocyclic base moiety" and "nucleobase" as used herein, include unmodified or naturally occurring nucleobases, modified or non-naturally occurring nucleobases as well as synthetic mimetics thereof (such as for example phenoxazines). In general, a heterocyclic base moiety is heterocyclic system that contains one or more atoms or groups of atoms capable of hydrogen bonding to a base of a nucleic acid.

As used herein the terms, "unmodified nucleobase" and "naturally occurring nucleobase" include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

The heterocyclic base moiety of each of the tetrahydropyran nucleoside analogs as provided herein can be modified with one or more substituent groups to enhance one or more properties such as affinity for a target strand or affect some other property in an advantageous manner. Modified nucleobases include without limitation, universal bases, hydrophobic bases, promiscuous bases, size-expanded bases, and fluorinated bases as defined herein. Certain of these nucleobases are particularly useful for increasing the binding affinity of the oligomeric compounds as provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (*Antisense Research and Applications*, Sanghvi, Y. S., Crooke, S. T. and Lebleu, B., Eds., CRC Press, Boca Raton, 1993, 276-278).

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

In general, the term "oligomeric compound" refers to a contiguous sequence of linked monomer subunits. In general, each linked monomer subunit is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups.

When preparing oligomeric compounds having specific motifs as disclosed herein it can be advantageous to mix non-naturally occurring monomer subunits such as the tetrahydropyran nucleoside analogs as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a tetrahydropyran nucleoside analog as provided herein. In certain embodiments, oligomeric compounds are provided comprising a plurality of tetrahydropyran nucleoside analogs as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [C(R)$_2$] or a heteroatom or substituted heteroatom (NR). Modified sugar moieties can also comprise mixtures of these modifications such as for example putting a 5'-substituent group on a bicyclic nucleoside.

Examples of substituent groups useful for modifying sugar moieties of nucleosides include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$, 2'-O(CH$_2$)$_2$SCH$_3$, 2'-O—CH$_2$—CH=CH$_2$ (MOE), 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_n$)(R$_n$)], 5'-vinyl, 5'-methyl (R or S) and 4'-S wherein each R$_m$ and R$_n$ is, independently, H, substituted or unsubstituted C$_1$-C$_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/ 101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

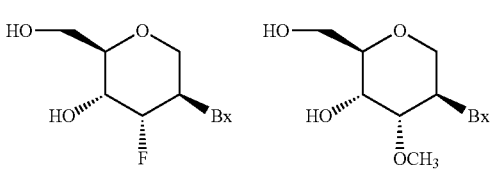

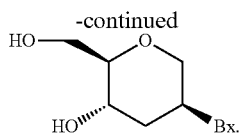

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the tetrahydropyran nucleoside analogs provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA:Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in Oligonucleotides and Analogues, a Practical Approach, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

As used herein the term "hybridization" includes the pairing of complementary strands of oligomeric compounds such as including the binding of an oligomeric compound as provided herein to a target nucleic acid. In certain embodiments, the mechanism of pairing involves hydrogen bonding, which may be Watson-Crick, Hoogsteen or reversed Hoogsteen hydrogen bonding, between complementary heterocyclic base moieties of nucleosides (or monomer subunits) that are in close enough proximity to hydrogen bond. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid resulting in a loss of activity. To be specifically hybridizable also requires a sufficient degree of complementarity to avoid non-specific binding of the oligomeric compound to non-target nucleic acid sequences under the conditions in which specific binding is desired, i.e., under physiological conditions (for in vivo assays or therapeutic treatment) or other diagnostic conditions (for performing in vitro assays).

As used herein the term "complementary," refers to the capacity for precise pairing of two nucleobases regardless of where the two nucleobases are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between an oligomeric compound and its target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806-811; Timmons and Fire, *Nature,* 1998, 395, 854; Timmons et al., *Gene,* 2001, 263, 103-112; Tabara et al., *Science,* 1998, 282, 430-431; Montgomery et al., *Proc. Natl. Acad. Sci. USA,* 1998, 95, 15502-15507; Tuschl et al., *Genes Dev.,* 1999, 13, 3191-3197; Elbashir et al., *Nature,* 2001, 411, 494-498; Elbashir et al., *Genes Dev.,* 2001, 15, 188-200). For example, such double-stranded moieties have been shown to inhibit the target by the classical hybridization of antisense strand of the duplex to the target, thereby triggering enzymatic degradation of the target (Tijsterman et al., *Science,* 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature,* 2001, 411, 494-498; Nishikura et al., *Cell,* 2001, 107, 415-416; and Bass et al., *Cell,* 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3-H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH₄OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., *J. Biol. Chem.* 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3-H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH₄OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments Involving Treatment of Cells with Oligomeric Compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 μg/mL per 100 nM oligomeric compound(s). This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTINT™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

Example 10

RNA Isolation

Poly(A)+ mRNA isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µl cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                        (SEQ ID NO: 2)
Forward primer: AATGGCTAAGTGAAGATGACAATCAT (SEQ ID NO: 3)
Reverse primer: TGCACATATCATTACACCAGTTCGT
```

And the PCR probe:

FAM-TTGCAGCAATTCACTGTAAAGCTG-GAAAGG-TAMRA (SEQ ID NO: 4_,where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 7 (Scheme 1)

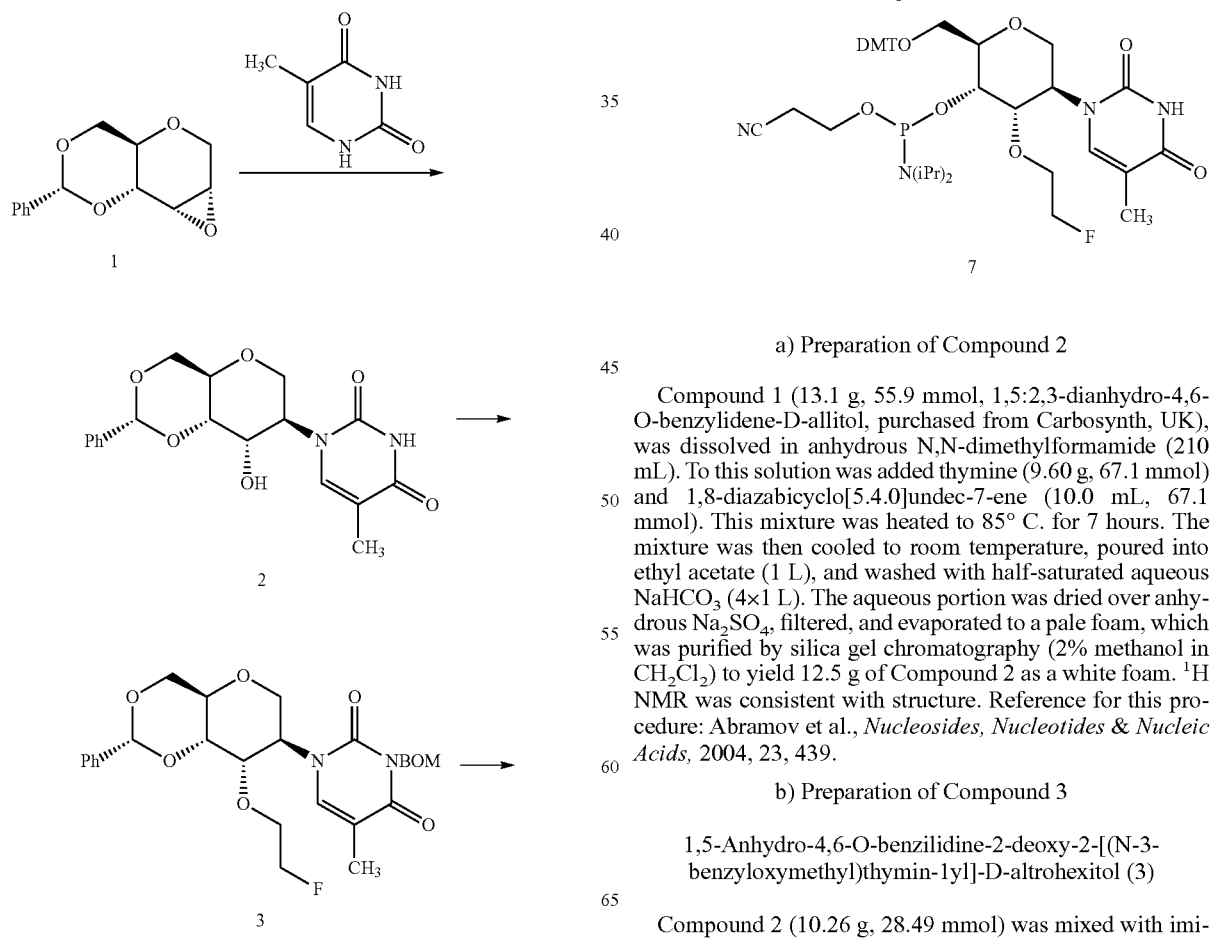

a) Preparation of Compound 2

Compound 1 (13.1 g, 55.9 mmol, 1,5:2,3-dianhydro-4,6-O-benzylidene-D-allitol, purchased from Carbosynth, UK), was dissolved in anhydrous N,N-dimethylformamide (210 mL). To this solution was added thymine (9.60 g, 67.1 mmol) and 1,8-diazabicyclo[5.4.0]undec-7-ene (10.0 mL, 67.1 mmol). This mixture was heated to 85° C. for 7 hours. The mixture was then cooled to room temperature, poured into ethyl acetate (1 L), and washed with half-saturated aqueous NaHCO$_3$ (4×1 L). The aqueous portion was dried over anhydrous Na$_2$SO$_4$, filtered, and evaporated to a pale foam, which was purified by silica gel chromatography (2% methanol in CH$_2$Cl$_2$) to yield 12.5 g of Compound 2 as a white foam. $^1$H NMR was consistent with structure. Reference for this procedure: Abramov et al., *Nucleosides, Nucleotides & Nucleic Acids*, 2004, 23, 439.

b) Preparation of Compound 3

1,5-Anhydro-4,6-O-benzilidine-2-deoxy-2-[(N-3-benzyloxymethyl)thymin-1yl]-D-altrohexitol (3)

Compound 2 (10.26 g, 28.49 mmol) was mixed with imidazole (7.76 g, 113.96 mmol) over P$_2$O$_5$ under reduced pressure. This mixture was dissolved in anhydrous DMF (60 mL) and chloro triethylsilane (8.59 g, 56.98 mmol) was added. The mixture was stirred at room temperature for 18 hours. The reaction mixture was diluted with EtOAc (200 mL), washed with sat. NaHCO$_3$ (500 mL) and brine (200 mL) then dried over anhydrous Na$_2$SO$_4$, filtered and evaporated. The residue was purified by silica gel column chromatography and eluted with 5% methanol, in CH$_2$Cl$_2$ to yield 3'-O-triethyl derivative of Compound 2 (13.42 g, 99%). Dissolved the silyl derivative (13.4 g, 28.25 mmol) in anhydrous DMF (120 mL). To this was added 1,8-diazabicycl-[5-4-0] undec-7-ene (DBU, 12.60 mL, 84.27 mmol) and the reaction mixture was cooled in an ice bath. Benzyl chloromethyl ether (5.89 mL, 42.42 mmol) was added with stirring at 0° C. for 1 hour. The mixture was diluted with EtOAc (200 mL), washed with aqueous NaHCO$_3$ (200 mL) and brine (200 mL) then dried (Na$_2$SO$_4$), filtered and evaporated. The residue obtained was dissolved in THF (100 mL) and triethylamine (8.77 mL, 63.00 mmol) and triethylaminetrihydro fluoride (20.54 mL, 126.15 mmol) were added. The reaction mixture was stirred at room temperature for 6 hours. The mixture was poured into EtOAc (200 mL), washed with water (200 mL), aqueous NaHCO$_3$ (saturated, 200 mL) and brine (200 mL) then dried over anhydrous Na$_2$SO$_4$, filtered and evaporated. The residue was purified by silica gel column chromatography and eluted with 50% EtOAc in hexane to yield Compound 3 (9.23 g, 71%) as a white foam. ES MS m/z 481.1 [M+H]$^+$.

c) Preparation of Compound 4

1,5-Anhydro-4,6-O-benzilidine-2-deoxy-2-[(N-3-benzyloxymethyl)thymin-1yl]-3-O-(2-fluoroethyl)-D-altro-hexitol (4)

Compound 3 (7.00 g, 14.57 mmol) was dried over P$_2$O$_5$ under reduced pressure and dissolved in anhydrous DMF (60 mL) under argon atmosphere. To this was added NaH (1.75 g, 43.70 mmol, 60% dispersion in mineral oil) with stirring for 30 minutes followed by addition of 2-fluoro-1-iodo-ethane (7.60 g, 43.70 mmol). After stirring for 1.5 hours at room temperature under argon atmosphere additional NaH (1.75 g, 43.70 mmol, 60% dispersion in mineral oil) was added. The stirring was continued for 30 minutes and 2-fluoro-1-iodo-ethane (7.60 g, 43.70 mmol) was added. Stirring was continued for another 30 minutes. The reaction was quenched with methanol (5 mL), diluted with EtOAc (200 mL), washed with water (100 mL) and brine (100 mL) then dried over Na$_2$SO$_4$, filtered and evaporated under reduced pressure. The residue was purified by silica gel column chromatography and eluted with 50% EtOAc in hexane to yield Compound 4 (7.37 g, 96%). ES MS m/z 527.2 [M+H]$^+$.

d) Preparation of Compound 5

2-deoxy-2-(thymin-1yl)-3-O-(2-fluoroethyl)-D-altro-hexitol (5)

Compound 4 (7.1 g, 13.48 mmol) was dissolved in MeOH (250 mL) and palladium hydroxide (3.50 g, 20 wt % Pd on carbon dry base) was added with stirring under an atmosphere of H$_2$ for 8 hours. Acetic acid (2.00 mL) was added with stirring for 5 minutes. The reaction mixture was filtered through a pad of celite 545, and the celite was washed with copious amounts of MeOH. The combined filtrate and washings were concentrated under reduced pressure and the residue was purified by silica gel column chromatography (5% methanol in CH$_2$Cl$_2$) to yield Compound 5 (4.27 g, 97%). ES MS m/z 319.1 [M+H]$^+$.

e) Preparation of Compound 6

6-O-(4,4'-dimethoxytrityl)-2-deoxy-2(thymin-1yl]-3-O-(2-fluoroethyl)D-altro-hexitol (6)

Compound 5 (4.07 g, 12.79 mmol) was mixed with 4,4'-dimethoxytrityl chloride (4.56 g, 13.46 mmol) and dried over P$_2$O$_5$ under reduced pressure. The residue was dissolved in anhydrous pyridine (43 mL) and stirred at room temperature for 6 hours under an atmosphere of argon. The mixture was quenched with methanol (3 mL). The reaction mixture was diluted with EtOAc (200 mL), washed with aqueous NaHCO$_3$ (saturated, 300 mL) and brine (200 mL) then dried over Na$_2$SO$_4$, filtered and concentrated. The residue obtained was purified by silica gel column chromatography (eluted first with 70% EtOAc in hexanes and then increasing the polarity) to yield Compound 6 (7.1 g, 89%). ES MS m/z 643.2 [M+Na]$^+$.

f) Preparation of Compound 7

6-O-(4,4'-dimethoxytrityl)-2-deoxy-2(thymin-1yl]-3-O-(2-fluoroethyl)-D-altro-hexitol-4-(2-cyanoethyl-N, N-diisopropylphosphoramidite) (7)

Compound 6 (1.33 g, 2.14 mmol) was dried over P$_2$O$_5$ under reduced pressure, then dissolved in anhydrous DMF (7 mL). 1-H-tetrazole (0.13 g, 1.83 mmol), N-methylimidazole (0.046 mL, 0.59 mmol) and 2-cyanoethyl-N,N,N',N'-tetraisopropylphosphorodiamidite (1.07 mL, 3.36 mmol) were then added. After 3 hours EtOAc (100 mL) was added and the mixture was washed with aqueous NaHCO$_3$ (100 mL) and brine (100 mL) then dried over anhydrous Na$_2$SO$_4$, filtered and evaporated in vacuo to give an oil. The oily residue was purified by silica gel column chromatography (60% EtOAc in hexanes) to yield Compound 7 (1.57 g, 89%) as a white foam. MS (ES): m/z 819.1 [M−H]$^-$. $^{31}$P NMR (121 MHz, CDCl$_3$): δ 150.3, 147.0; $^{19}$F NMR (282 MHz, CDCl$_3$) δ −223.5 to −224.2 (19F-$^1$H coupled, m).

Example 14

Preparation of Compound 11 (Scheme 2)

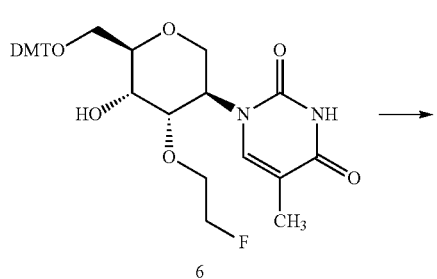

6 b) Preparation of Compound 9

6-O-(4,4'-dimethoxytrityl)-3-O-(2-fluoroethyl)-4-O-(triethylsilyl)-2-deoxy-2-(5-methylcytosin-1yl)-D-altro-hexitol (9)

A suspension of 1,2,4-triazole (7.35 g, 106.42 mmol) in anhydrous $CH_3CN$ (41 mL) was cooled in an ice bath for 5 to 10 minutes under an atmosphere of argon. To this cold suspension, $POCl_3$ (2.31 mL, 24.82 mmol) was added slowly over 10 minutes with stirring continued for an additional 5 minutes. Triethylamine (17.40 mL, 124.77 mmol) was added slowly over 30 minutes, keeping the bath temperature at about 0-2° C. The reaction mixture was stirred at 0-2° C. for an additional 30 minutes. Compound 8 (2.31 g, 3.13 mmol) in anhydrous $CH_3CN$ (20.7 mL) was added in one portion and stirred for 10 minutes. The reaction mixture was removed from the ice bath and stirred at room temperature for 4 hours under an atmosphere of argon. The mixture was concentrated to one third of its volume, diluted with ethyl acetate (100 mL), and washed with water (2×100 mL) and brine (100 mL). The organic phase was dried over anhydrous $Na_2SO_4$ and concentrated under reduced pressure. The resulting residue was dissolved in a solution of aqueous $NH_3$ (18.3 mL, 28-30 wt %) and dioxane (45 mL). The reaction mixture was stirred at room temperature overnight in a pressure bottle. The solvent was removed in vacuum and the resulting residue was purified by flash silica gel column chromatography (5% MeOH in $CH_2Cl_2$) to yield Compound 9 (2.04 g, 88.3%) as a white foam. MS (ES) m/z 734.3 $[M+H]^+$.

c) Preparation of Compound 10

6-O-(4,4'-dimethoxytrityl)-3-O-(2-fluoroethyl)-2-deoxy-2-(4-N-benzoyl-5-methyl-cytosin-1yl)-D-altro-hexitol (10)

Compound 9 (1.92 g, 2.58 mmol) was dissolved in anhydrous DMF (11.9 mL) and benzoic anhydride (0.87 g, 3.85 mmol) was added with stirring at room temperature for 18 hours. The reaction mixture was diluted with ethyl acetate (100 mL) and the resulting organic phase was washed with a saturated aqueous $NaHCO_3$ (2×100 mL) and brine (100 mL). The ethyl acetate layer was dried over anhydrous $Na_2SO_4$ and concentrated in vacuum. The residue obtained was purified by flash silica gel column chromatography and eluted with 60% ethyl acetate in hexane to yield 6-O-(4,4'-dimethoxytrityl)-3-O-(2-fluoroethyl)-4-O-(triethylsilyl)-2-deoxy-244-N-benzoyl-5-methylcytosin-1yl)-D-altro-hexitol (2.04 g, 93.2%). In a 100 mL round bottom flask, triethylamine trihydrofluoride (2.04 mL, 12.55 mmol) was dissolved in anhydrous THF (23.2 mL). Triethylamine (0.87 mL, 6.28 mmol) was added to this solution, and the mixture was quickly poured onto 6-O-(4,4'-dimethoxytrityl)-3-O-(2-fluoroethyl)-4-O-(triethylsilyl)-2-deoxy-2-(4-N-benzoyl-5-methylcytosin-1yl)-D-altro-hexitol (2.04 g, 2.44 mmol). The resulting mixture was stirred at room temperature for 6 hours and then poured into ethyl acetate (80 mL). The organic phase was washed sequentially with water (50 mL), 5% aqueous $NaHCO_3$ (50 mL) and brine (50 mL). The ethyl acetate layer was dried over anhydrous $Na_2SO_4$, filtered and concentrated in vacuum under reduced pressure. The residue obtained was purified by silica gel column chromatography (30% ethyl acetate in hexanes) to afford compound 10 (1.66 g, 87.94%) as a white foam. MS (ES) m/z 724.3 $[M+H]^+$.

a) Preparation of Compound 8

6-O-(4,4'-dimethoxytrityl)-3-O-(2-fluoroethyl)-4-O-(triethylsilyl)-2-deoxy-2-(thymin-1yl)-D-altro-hexitol (8)

Compound 6, prepared as per the procedures illustrated in Example 13 (2.50 g, 4.00 mmol) was mixed with imidazole (1.36 g, 20.0 mmol) over $P_2O_5$ under reduced pressure. This mixture was dissolved in anhydrous DMF (13 mL) and chloro triethylsilane (1.71 mL, 10 mmol) was added. The mixture was stirred at room temperature for 12 hours. The reaction mixture was diluted in EtOAc (100 mL), washed with sat. $NaHCO_3$ (100 mL) and brine (50 mL) then dried over anhydrous $Na_2SO_4$, filtered and evaporated. The residue was purified by silica gel column chromatography (50% EtOAc in hexanes) to yield Compound 8 (2.45 g, 82.5%) as a white foam. MS (ES): m/z 760.2 $[M+Na]^+$.

d) Preparation of Compound 11

6-O-(4,4'-dimethoxytrityl)-3-O-(2-fluoroethyl)-2-deoxy-2-(4-N-benzoyl-5-methyl-cytosin-1yl)-D-altro-hexitol-4-(2-cyanoethyl-N,N-diisopropylphosphoramidite) (11)

Compound 10 (1.53 g, 2.12 mmol) was dried over $P_2O_5$ under reduced pressure, then dissolved in anhydrous DMF (7 mL). 1-H-tetrazole (0.13 g, 1.85 mmol), N-methylimidazole (0.045 mL, 0.58 mmol) and 2-cyanoethyl-N,N,N',N'-tetraisopropylphosphorodiamidite (1.05 mL, 3.31 mmol) were added. After 4 hours EtOAc (80 mL) was added and the reaction mixture was washed with saturated $NaHCO_3$ (70 mL) and brine (50 mL) then dried over anhydrous $Na_2SO_4$, filtered and evaporated under reduced pressure to give an oil. The oily residue was purified the by silica gel column chromatography (50% EtOAc in hexanes) to yield Compound 11 (1.72 g, 88.21%) as a white form. MS (ES): m/z 922.4 [M–H]⁻. $^{31}P$ NMR (121 MHz, $CDCl_3$): δ 150.4, 147.3; $^{19}F$ NMR (282 MHz, $CDCl_3$). δ –223.5 to –224.2 (19F-$^1H$ coupled, m).

Example 15

Preparation of Compound 15 (Scheme 3)

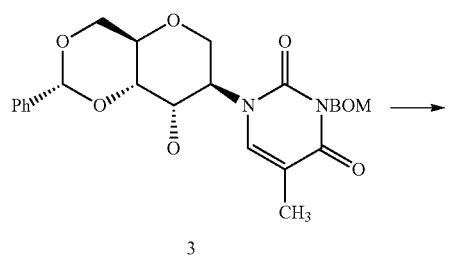

3

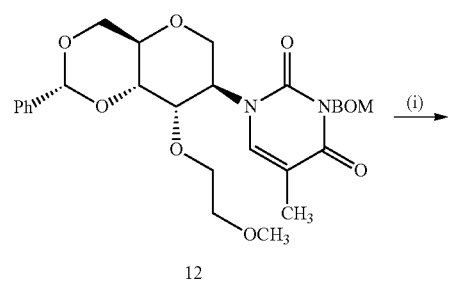

12

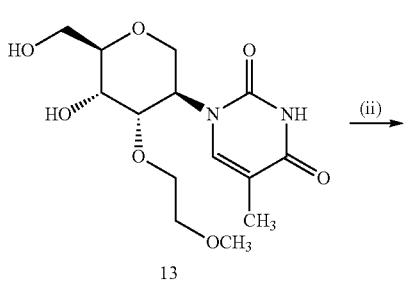

13

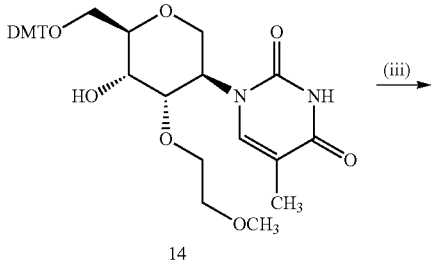

14

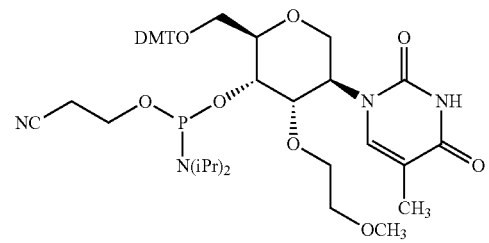

15

Scheme 3.
(i) palladium hydroxide, methanol, $H_2$, acetic acid;
(ii) 4,4'–dimethoxytrityl chloride, pyridine, rt;
(iii) cyanoethyl-N,N,N'N'–tetraiso-propylphosphorodiamidite, 1-H-tetrazole, N-methylimidazole, DMF.

a) Preparation of Compound 12

1,5-Anhydro-4,6-O-benzilidine-2-deoxy-2-[(N-3-benzyloxymethyl)thymin-1yl]-3-O-(2-methoxyethyl)-D-altro-hexitol (12)

Compound 3, prepared as per the procedures illustrated in Example 13 (0.25 g, 0.52 mmol) was dried over $P_2O_5$ under reduced pressure and then dissolved in anhydrous DMF (2 mL) under an atmosphere of argon. NaH (0.06 g, 1.6 mmol, 60% dispersion in mineral oil) was added with stirring for 30 minutes followed by addition of 1-iodo-2-methoxyethane (0.15 g, 1.60 mmol). After stirring for 3 hours at room temperature under an atmosphere of argon the reaction was quenched with methanol (0.2 mL), diluted with EtOAc (20 mL), washed with water (15 mL) and brine (15 mL) then dried over $Na_2SO_4$, filtered and evaporated under reduced pressure. The residue was purified by silica gel column chromatography (50% EtO in hexanes) to yield Compound 12 (0.18 g, 64.3%). ES MS m/z 539.2 [M+H]⁺.

b) Preparation of Compound 15

Compound 15 was prepared as per the procedure illustrated in Example 13 starting from Compound 12. Spectral data (including $^1H$ NMR) was consistent with structure.

Example 16

Preparation of Compound 19 (Scheme 4)

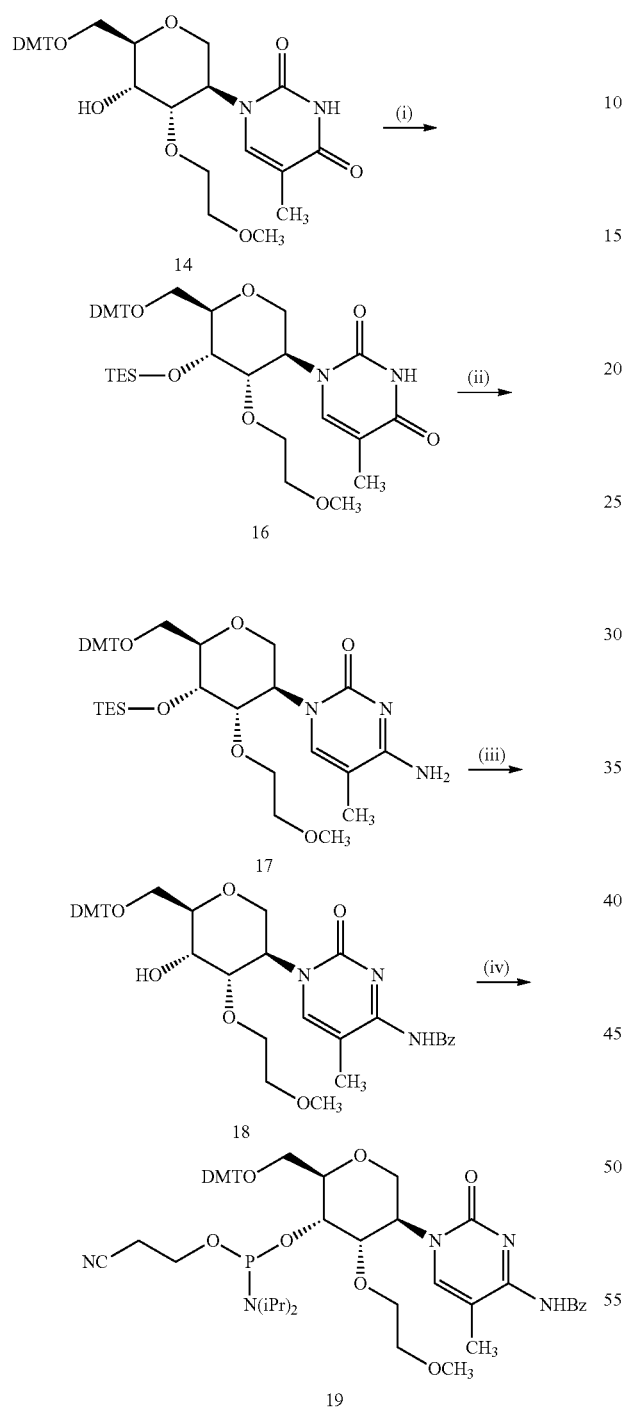

Scheme 4. TES: triethylsilyl; Bz: benzoyl;
(i) a. chlorotriethylsilane, imidazole, DMF, rt;
(ii) a. triethyl amine, 1,2,4-tetrazole, CH₃CN, POCl₃ b. NH₄OH-dioxane;
(iii) a. benzoic anhydride, DMF, rt, b. triethylamine trihydrofluoride, triethylamine, THF, rt;
(iv) cyano-ethyl-N,N,N'N'-tetraospropylphosphorodiamidite, 1-H-tetrazole, N-methylimidazole, DMF.

Compounds 14 and 19 were prepared as per the procedures illustrated in examples 15 and 14, respectively. Spectral data (including ¹H NMR) was consistent with structure.

Example 17

Preparation of Compound 23 (Scheme 5)

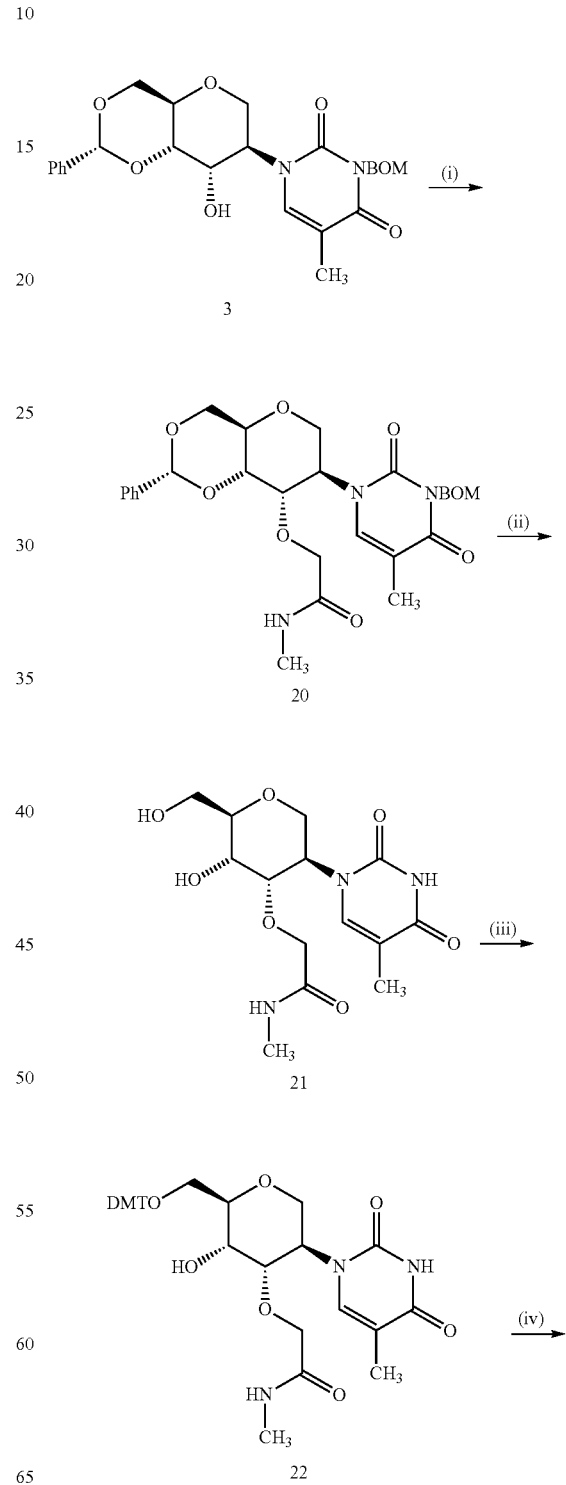

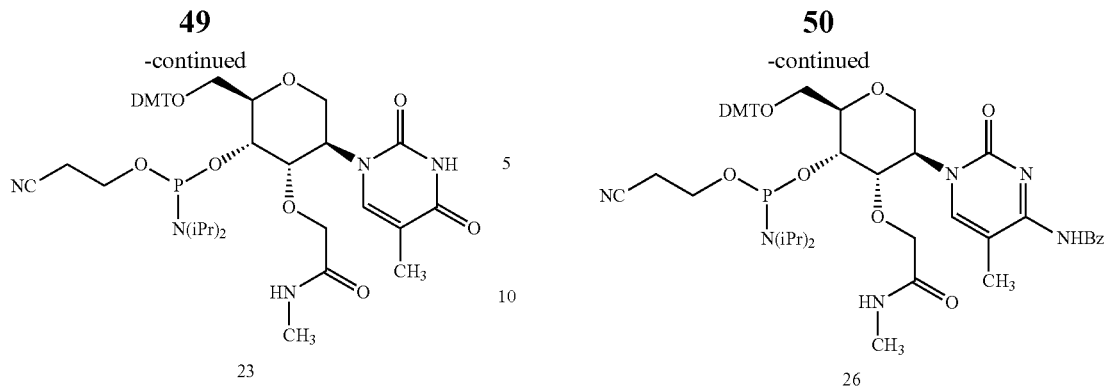

Scheme 5.
(i) a. NaH, DMF, ethyl iodoacetate, rt, b. N-methylamine, THF;
(ii) palladium hydroxide, methanol, H₂, acetic acid;
(iii) 4,4′-dimethoxytrityl chloride, pyridine, rt;
(iv) cyanoethyl-N,N,N′N′-tetraisopropylphosphorodiamidite, 1-H-tetrazole, N-methylimidazole, DMF.

Compound 3 is prepared as per the procedures illustrated in Example 13.

Example 18

Preparation of Compound 26 (Scheme 6)

Scheme 6.
(i) a. chlorotriethylsilane, imidazole, DMF, rt;
(ii) a. triethyl amine, 1,2,4-tetrazole, CH₃CN, POCl₃ b. NH₄OH-dioxane;
(iii) a. benzoic anhydride, DMF, rt, b. triethylamine trihydrofluoride, triethylamine, THF, rt;
(iv) cyano-ethyl-N,N,N′N′-tetraisopropylphosphorodiamidite, 1-H-tetrazole, N-methyl-imidazole, DMF.

Compound 22 is prepared as per the procedures illustrated in Example 17.

Example 19

Preparation of Compound 38 (Scheme 7)

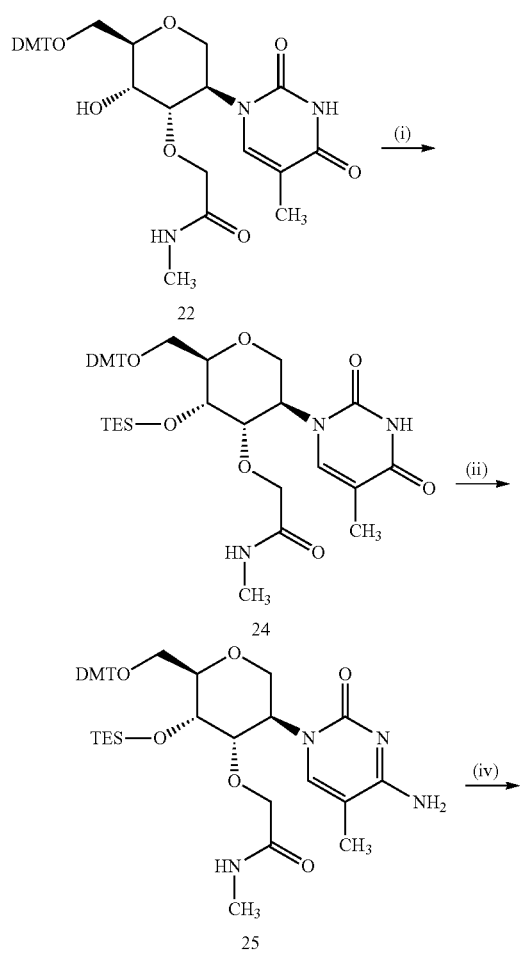

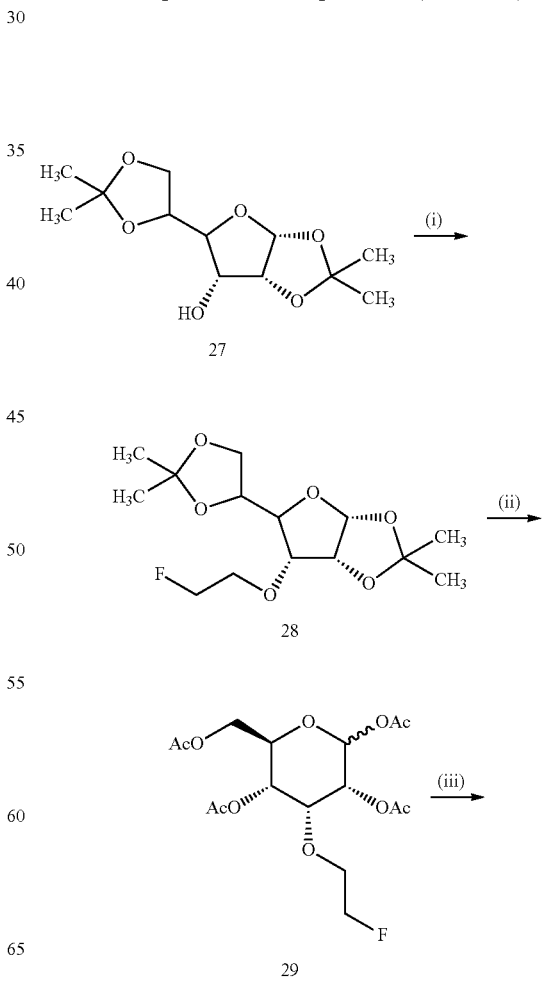

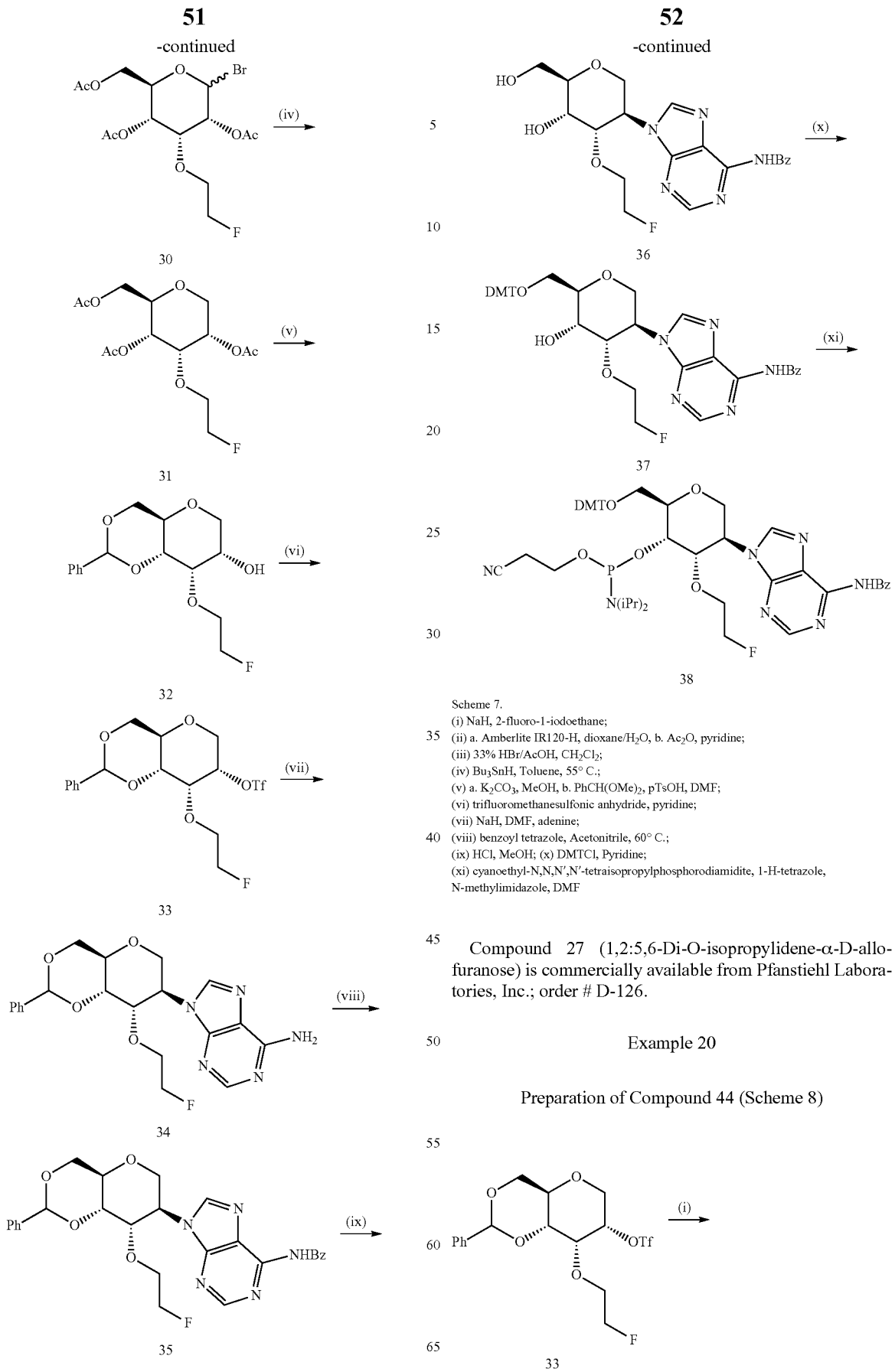

Scheme 7.
(i) NaH, 2-fluoro-1-iodoethane;
(ii) a. Amberlite IR120-H, dioxane/H$_2$O, b. Ac$_2$O, pyridine;
(iii) 33% HBr/AcOH, CH$_2$Cl$_2$;
(iv) Bu$_3$SnH, Toluene, 55° C.;
(v) a. K$_2$CO$_3$, MeOH, b. PhCH(OMe)$_2$, pTsOH, DMF;
(vi) trifluoromethanesulfonic anhydride, pyridine;
(vii) NaH, DMF, adenine;
(viii) benzoyl tetrazole, Acetonitrile, 60° C.;
(ix) HCl, MeOH; (x) DMTCl, Pyridine;
(xi) cyanoethyl-N,N,N',N'-tetraisopropylphosphorodiamidite, 1-H-tetrazole, N-methylimidazole, DMF Compound 27 (1,2:5,6-Di-O-isopropylidene-α-D-allofuranose) is commercially available from Pfanstiehl Laboratories, Inc.; order # D-126.

Example 20

Preparation of Compound 44 (Scheme 8)

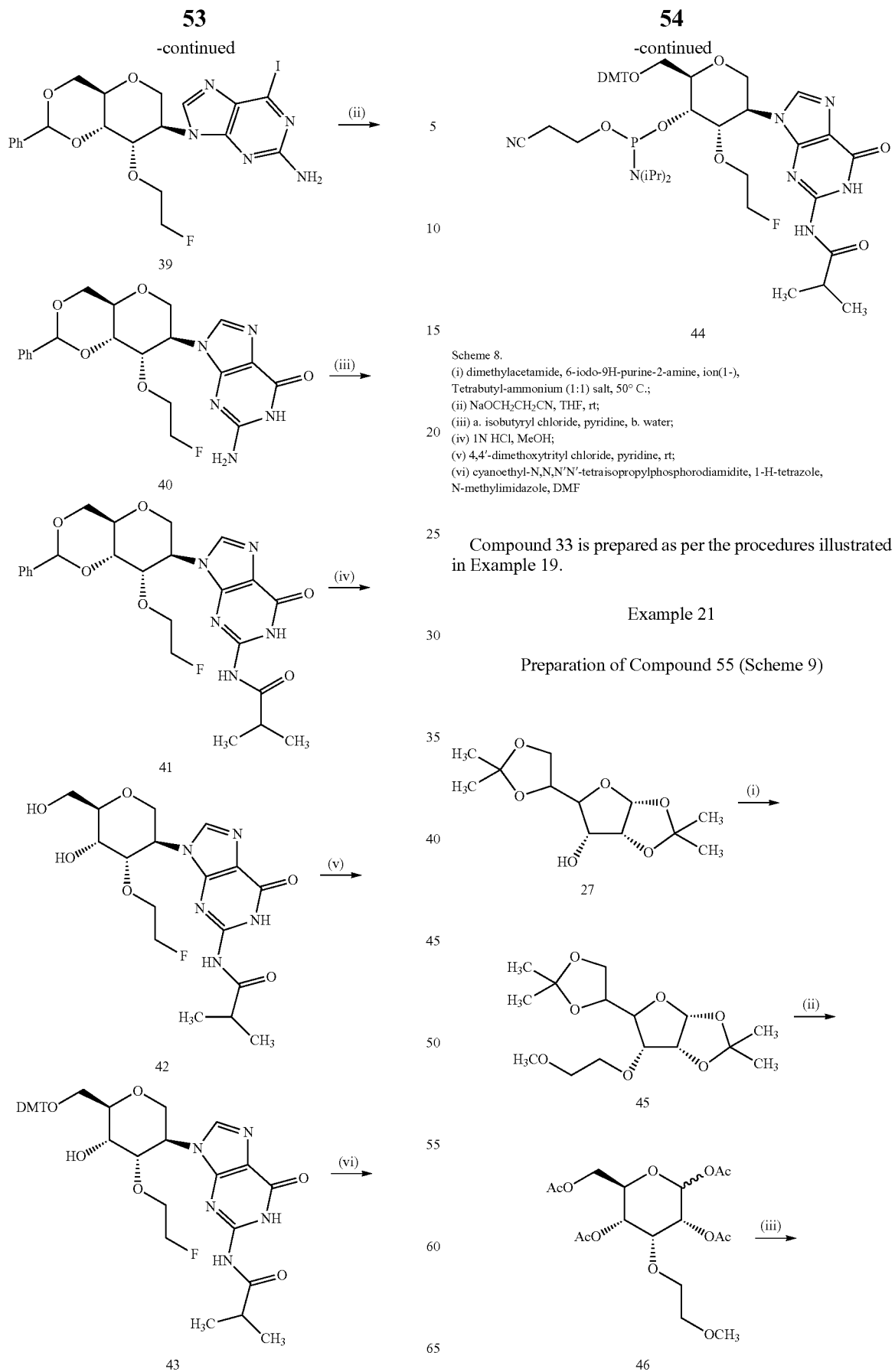

Scheme 8.
(i) dimethylacetamide, 6-iodo-9H-purine-2-amine, ion(1-), Tetrabutyl-ammonium (1:1) salt, 50° C.;
(ii) NaOCH₂CH₂CN, THF, rt;
(iii) a. isobutyryl chloride, pyridine, b. water;
(iv) 1N HCl, MeOH;
(v) 4,4′-dimethoxytrityl chloride, pyridine, rt;
(vi) cyanoethyl-N,N,N′N′-tetraisopropylphosphorodiamidite, 1-H-tetrazole, N-methylimidazole, DMF Compound 33 is prepared as per the procedures illustrated in Example 19.

Example 21

Preparation of Compound 55 (Scheme 9)

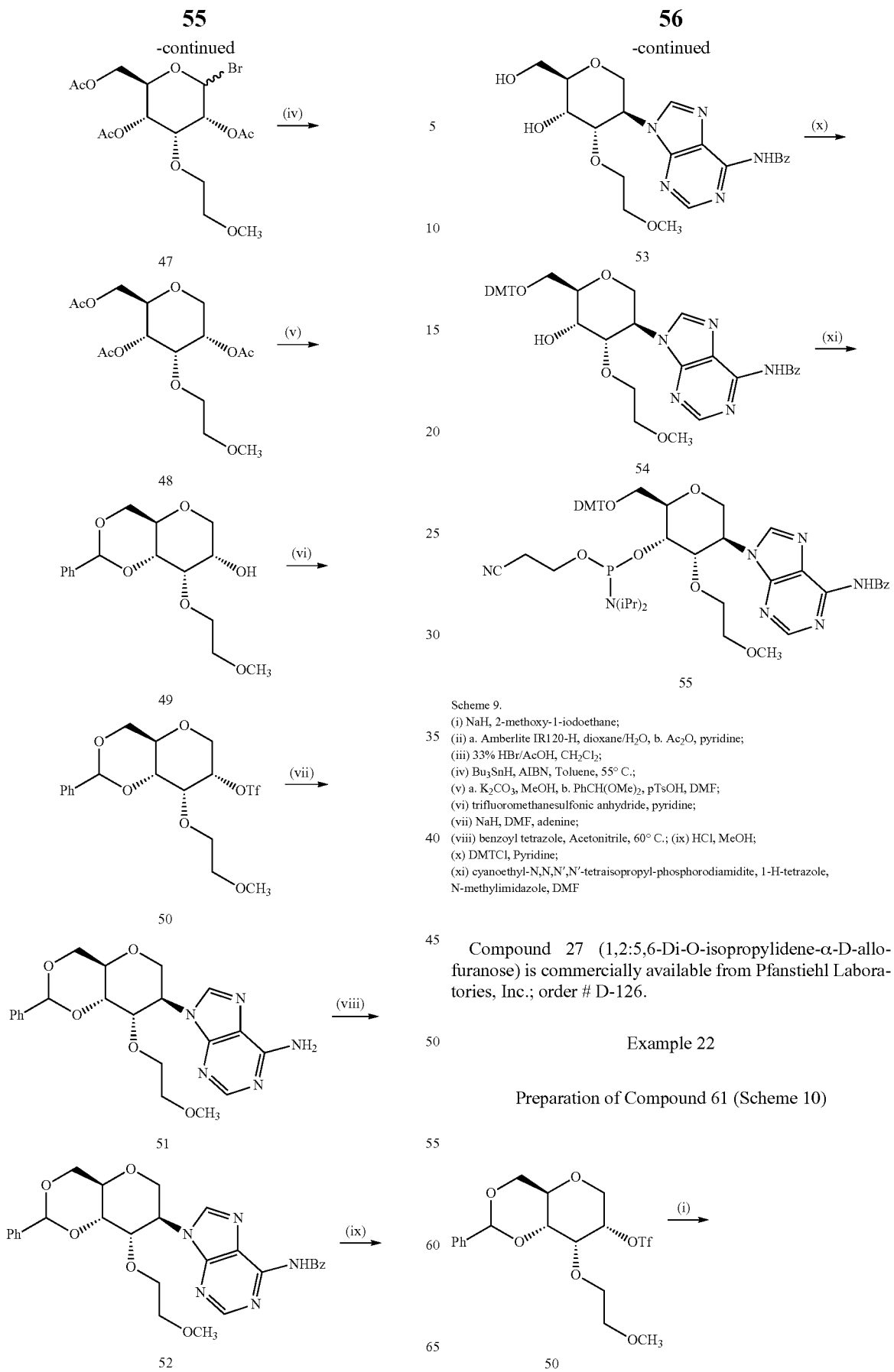

Scheme 9.
(i) NaH, 2-methoxy-1-iodoethane;
(ii) a. Amberlite IR120-H, dioxane/H$_2$O, b. Ac$_2$O, pyridine;
(iii) 33% HBr/AcOH, CH$_2$Cl$_2$;
(iv) Bu$_3$SnH, AIBN, Toluene, 55° C.;
(v) a. K$_2$CO$_3$, MeOH, b. PhCH(OMe)$_2$, pTsOH, DMF;
(vi) trifluoromethanesulfonic anhydride, pyridine;
(vii) NaH, DMF, adenine;
(viii) benzoyl tetrazole, Acetonitrile, 60° C.; (ix) HCl, MeOH;
(x) DMTCl, Pyridine;
(xi) cyanoethyl-N,N,N',N'-tetraisopropyl-phosphorodiamidite, 1-H-tetrazole, N-methylimidazole, DMF Compound 27 (1,2:5,6-Di-O-isopropylidene-α-D-allofuranose) is commercially available from Pfanstiehl Laboratories, Inc.; order # D-126.

Example 22

Preparation of Compound 61 (Scheme 10)

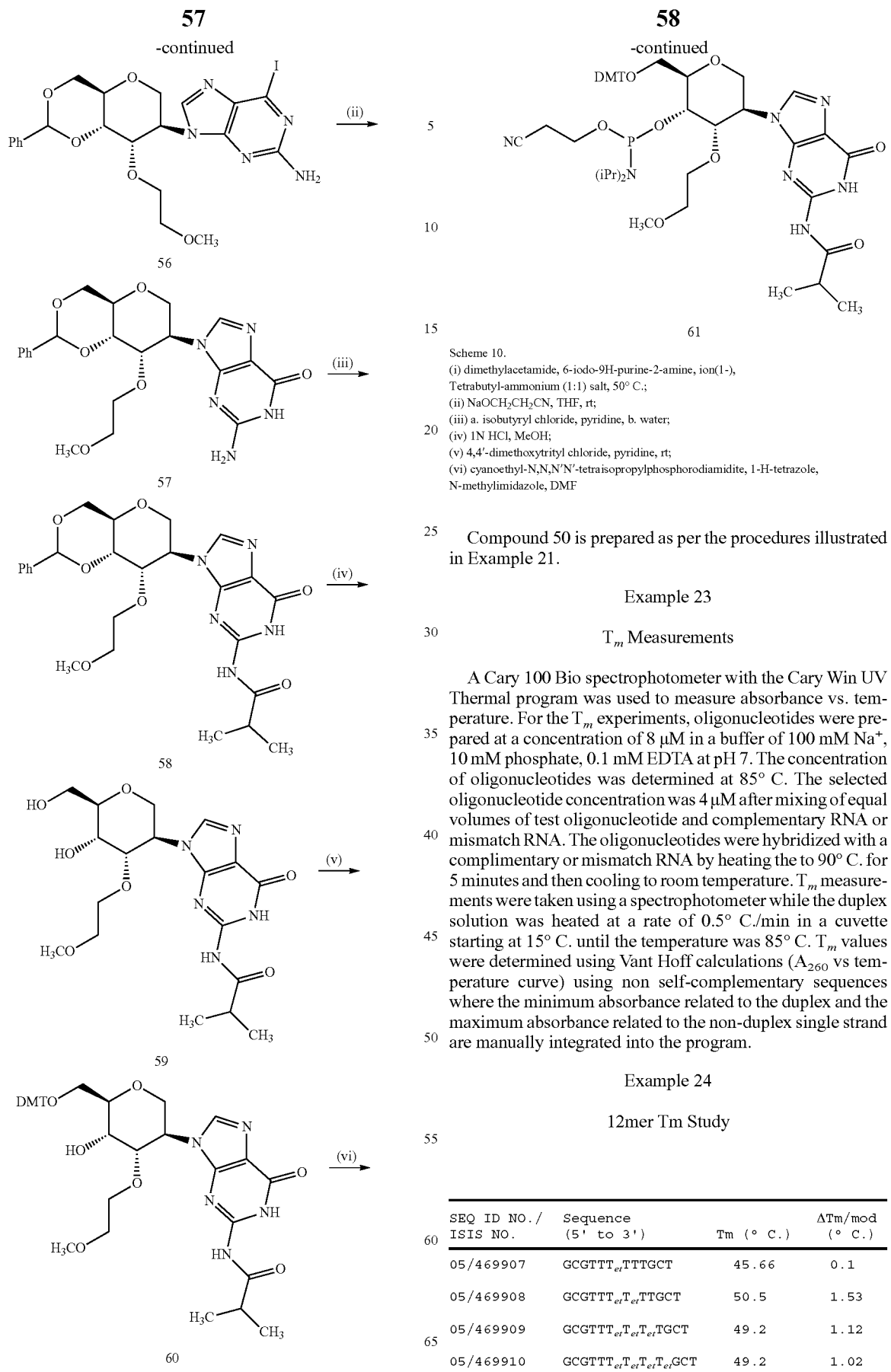

Scheme 10.
(i) dimethylacetamide, 6-iodo-9H-purine-2-amine, ion(1-), Tetrabutyl-ammonium (1:1) salt, 50° C.;
(ii) NaOCH₂CH₂CN, THF, rt;
(iii) a. isobutyryl chloride, pyridine, b. water;
(iv) 1N HCl, MeOH;
(v) 4,4′-dimethoxytrityl chloride, pyridine, rt;
(vi) cyanoethyl-N,N,N′N′-tetraisopropylphosphorodiamidite, 1-H-tetrazole, N-methylimidazole, DMF Compound 50 is prepared as per the procedures illustrated in Example 21.

Example 23

$T_m$ Measurements

A Cary 100 Bio spectrophotometer with the Cary Win UV Thermal program was used to measure absorbance vs. temperature. For the $T_m$ experiments, oligonucleotides were prepared at a concentration of 8 μM in a buffer of 100 mM Na⁺, 10 mM phosphate, 0.1 mM EDTA at pH 7. The concentration of oligonucleotides was determined at 85° C. The selected oligonucleotide concentration was 4 μM after mixing of equal volumes of test oligonucleotide and complementary RNA or mismatch RNA. The oligonucleotides were hybridized with a complimentary or mismatch RNA by heating the to 90° C. for 5 minutes and then cooling to room temperature. $T_m$ measurements were taken using a spectrophotometer while the duplex solution was heated at a rate of 0.5° C./min in a cuvette starting at 15° C. until the temperature was 85° C. $T_m$ values were determined using Vant Hoff calculations ($A_{260}$ vs temperature curve) using non self-complementary sequences where the minimum absorbance related to the duplex and the maximum absorbance related to the non-duplex single strand are manually integrated into the program.

Example 24

12mer Tm Study

| SEQ ID NO./ ISIS NO. | Sequence (5' to 3') | Tm (° C.) | ΔTm/mod (° C.) |
|---|---|---|---|
| 05/469907 | GCGTTT$_{et}$TTTGCT | 45.66 | 0.1 |
| 05/469908 | GCGTTT$_{et}$T$_{et}$TTGCT | 50.5 | 1.53 |
| 05/469909 | GCGTTT$_{et}$T$_{et}$T$_{et}$TGCT | 49.2 | 1.12 |
| 05/469910 | GCGTTT$_{et}$T$_{et}$T$_{et}$T$_{et}$GCT | 49.2 | 1.02 |

| SEQ ID NO./ ISIS NO. | Sequence (5' to 3') | Tm (° C.) | ΔTm/mod (° C.) |
|---|---|---|---|
| 05/472146 | GCGTTT$_{ef}$TTTGCT | 48.12 | 2.6 |
| 05/472147 | GCGTTT$_{ef}$T$_{ef}$TTGCT | 50.38 | 2.4 |
| 05/469909 | GCGTTT$_{ef}$T$_{ef}$T$_{ef}$TGCT | 52.19 | 2.2 |
| 05/469910 | GCGTTT$_{ef}$T$_{ef}$T$_{ef}$T$_{ef}$GCT | 50.83 | 1.3 |
| 05/438705 | GCGTTTTTGCT | 45.55 | — |

Each internucleoside linkage is a phosphodiester. Nucleosides not followed by a subscript are β-D-2'-deoxyribonucleosides. The nucleosides with subscript "et" or "ef" are defined below wherein each Bx is a heterocyclic base.

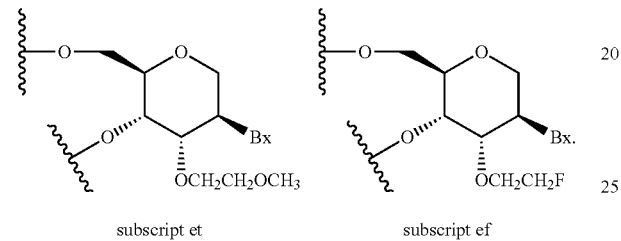

subscript et      subscript ef

Example 25

Tm Study

Tm's were determined in 100 mM phosphate buffer, 0.1 mM EDTA, pH 7, at 260 nm using 4 μM of each of the oligomeric compounds listed below and 4 μM of complementary RNA.

| SEQ ID NO./ ISIS NO. | Sequence (5' to 3') | Tm (° C.) vs. 14-mer RNA | Tm (° C.) vs. 20-mer RNA |
|---|---|---|---|
| 06/425857 | $^{Me}$C$_h$T$_h$TAGCACTGGC$^{Me}$C$_h$T$_h$ | 54.9 | 58.0 |
| 06/417999 | $^{Me}$C$_{ft}$T$_{ft}$TAGCACTGGC$^{Me}$C$_{ft}$T$_{ft}$ | 53.9 | 60.1 |
| 06/447585 | $^{Me}$C$_{ef}$T$_{ef}$TAGCACTGGC$^{Me}$C$_{ef}$T$_{ef}$ | 51.4 | 57.7 |
| 07/410312 | C$_{mt}$U$_{mt}$TAGCACTGGCC$_{mt}$U$_{mt}$ | 48.9 | 53.8 |
| 06/418857 | CTTAGCACTGGCCT | 48.5 | 52.1 |

Each internucleoside linkage is a phosphorothioate. Nucleosides not followed by a subscript are β-D-2'-deoxyribonucleosides. Superscript "Me" indicates a 5-methyl group on the pyrimidine base. Subscripted nucleosides are defined below wherein Bx is a heterocyclic base:

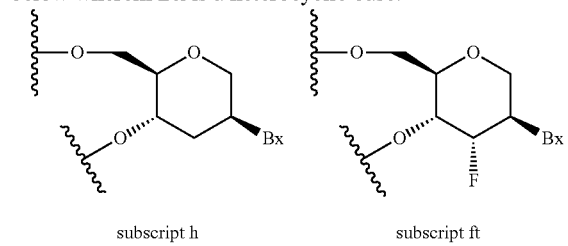

subscript h      subscript ft subscript ef      subscript mt

Example 26

PTEN Multiple Administration In Vivo Study

Six week old Balb/c mice (Jackson Laboratory, Bar Harbor, Me.) were injected twice per week for three weeks with the selected oligomeric compounds targeting PTEN at a dose of 0.47, 1.5, 4.7 or 15 mg/kg for ISIS 417999; 0.79, 2.5, 7.9 or 25 mg/kg for 447585, and 0.5, 1.5, 5.0 or 15 mg/kg for 413058. The mice were sacrificed 48 hours following last administration. Liver tissues were homogenized and mRNA levels were quantitated using real-time PCR as described herein for comparison to untreated control levels (% UTC). Plasma chemistry analysis was completed. The results are listed below as the average % of PTEN mRNA expression for each treatment group relative to saline-injected control.

| SEQ. ID NO./ ISIS NO. | Composition (5' to 3') | ED$_{50}$ (mg/kg) |
|---|---|---|
| 06/417999 | $^{Me}$C$_{ft}$T$_{ft}$TAGCACTGGC$^{Me}$C$_{ft}$T$_{ft}$ | 2.1 |
| 06/447585 | $^{Me}$C$_{ef}$T$_{ef}$TAGCACTGGC$^{Me}$C$_{ef}$T$_{ef}$ | 15.8 |
| 06/413058 | $^{Me}$C$_x$T$_x$TAGCACTGGC$^{Me}$C$_x$T$_x$ | 13 |

Each internucleoside linkage is a phosphorothioate. Nucleosides not followed by a subscript are β-D-2'-deoxyribonucleosides. Superscript "Me" indicates a 5-methyl group on the pyrimidine base of the nucleoside. Subscripted nucleosides are defined below wherein Bx is a heterocyclic base:

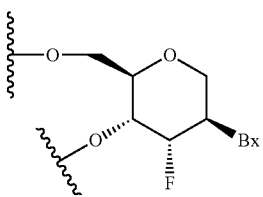

subscript ft

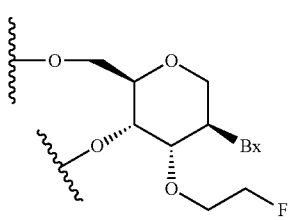

subscript ef

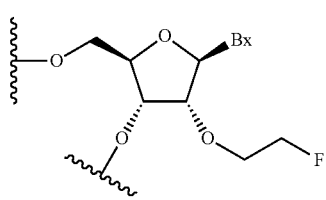

subscript x

| SEQ ID NO. / ISIS NO. | % UTC at dosage | | | |
|---|---|---|---|---|
| 06/417999 | 0.47 mg/kg | 1.5 mg/kg | 4.7 mg/kg | 15 mg/kg |
| | 77 | 64 | 31 | 10 |
| 06/413058 | 0.5 mg/kg | 1.5 mg/kg | 5.0 mg/kg | 15 mg/kg |
| | 93 | 76.7 | 78.4 | 43.2 |

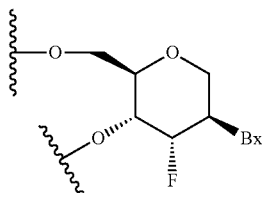

subscript ft

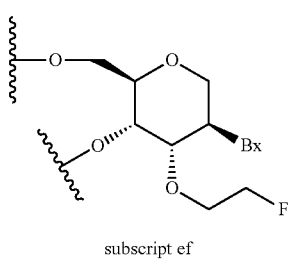

subscript ef

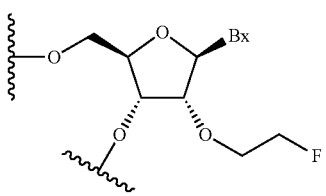

subscript x

| SEQ ID NO. / ISIS NO. | % UTC at dosage | | | |
|---|---|---|---|---|
| 06/447585 | 0.79 mg/kg | 2.5 mg/kg | 7.9 mg/kg | 25 mg/kg |
| | 95.1 | 89.4 | 73.4 | 33.5 |

Saline: % UTC = 100.

Liver transaminase levels, alanine aminotranferease (ALT) and aspartate aminotransferase (AST), in serum were measured relative to saline injected mice and no substantial changes were observed. The body weights, liver weights, spleen weights and kidney weights were measured at the different doses with no substantial deviations compared to the saline treated animals for ISIS 447585.

What is claimed is:

1. A tetrahydropyran nucleoside analog having Formula I:

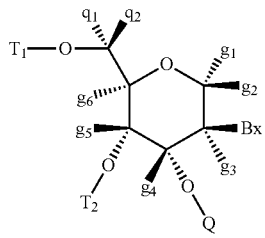

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group selected from a phosphoramidite, an H-phosphonate, a phosphate triester or a phosphorus containing chiral auxiliary;
Q is $CH_2F$, $CHF_2$, $CF_3$, $CH_2CH_2F$, $CH_2CHF_2$, $CH_2CF_3$, or $CH_2C(=O)N(H)CH_3$;
$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H or $C_1$-$C_6$ alkyl, and L is O, S or $NJ_1$.

2. The tetrahydropyran nucleoside analog of claim 1 wherein $g_1$, $g_2$, $g_3$, $g_4$, $g_5$, and $g_6$ are each H.

3. The tetrahydropyran nucleoside analog of claim 1 wherein $q_1$ and $q_2$ are each H.

4. The tetrahydropyran nucleoside analog of claim 1 wherein $q_1$ is methyl and $q_2$ is H or $q_2$ is methyl and $q_1$ is H.

5. The tetrahydropyran nucleoside analog of claim 1 wherein Bx is uracil, thymine, cytosine, 5-methylcytosine, adenine or guanine.

6. The tetrahydropyran nucleoside analog of claim 1 wherein $T_1$ is selected from acetyl, benzyl, t-butyldimethylsilyl, t-butyldiphenylsilyl and dimethoxytrityl.

7. The tetrahydropyran nucleoside analog of claim 1 wherein $T_1$ is 4,4'-dimethoxytrityl and $T_2$ is diisopropylcyanoethoxy phosphoramidite.

8. The tetrahydropyran nucleoside analog of claim 1 wherein Q is $CH_2CH_2F$ or $CH_2C(=O)N(H)CH_3$.

9. An oligomeric compound comprising at least one tetrahydropyran nucleoside analog of Formula II:

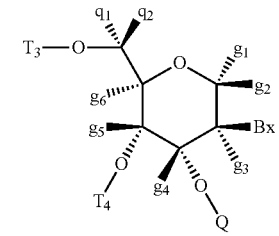

wherein independently for each of said at least one tetrahydropyran nucleoside analog of Formula II:
Bx is a heterocyclic base moiety capable of hydrogen bonding to a complementary heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group or a 5' or 3'-terminal group;
Q is $CH_2F$, $CHF_2$, $CF_3$, $CH_2CH_2F$, $CH_2CHF_2$, $CH_2CF_3$, or $CH_2C(=O)N(H)CH_3$;
$q_1$ and $q_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$g_1$, $g_2$, $g_3$, $g_4$, $g_5$, and $g_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H or $C_1$-$C_6$ alkyl, and L is O, S or $NJ_1$.

10. The oligomeric compound of claim 9 wherein each $g_1$, $g_2$, $g_3$, $g_4$, $g_5$, and $g_6$ is H for each of said at least one tetrahydropyran nucleoside analog of Formula II.

11. The oligomeric compound of claim 9 wherein $q_1$ and $q_2$ are each H for each of said at least one tetrahydropyran nucleoside analog of Formula II.

12. The oligomeric compound of claim 9 wherein $q_1$ is methyl and $q_2$ is H, or $q_2$ is methyl and $q_1$ is H for each of said at least one tetrahydropyran nucleoside analog of Formula II.

13. The oligomeric compound of claim 9 wherein Q is $CH_2CH_2F$ or $CH_2C(=O)N(H)CH_3$ for each of said at least one tetrahydropyran nucleoside analog of Formula II.

14. The oligomeric compound of claim 9 comprising at least one region having at least 2 contiguous tetrahydropyran nucleoside analogs of Formula II.

15. The oligomeric compound of claim 9 comprising at least two regions wherein each region independently comprises from 1 to about 5 contiguous tetrahydropyran nucleoside analogs of Formula II and wherein the two regions are separated by an internal region comprising at least one monomer subunit wherein each monomer subunit in the internal region is, independently, a nucleoside or a modified nucleoside.

16. The oligomeric compound of claim 15 comprising a gapped oligomeric compound wherein one of said at least two regions of contiguous tetrahydropyran nucleoside analogs of Formula II is located at the 5'-end and the other of said at least two regions of contiguous tetrahydropyran nucleoside analogs of Formula II is located at the 3'-end and wherein the two regions are separated by an internal region comprising from about 6 to about 18 monomer subunits wherein each monomer subunit is, independently, a nucleoside or a modified nucleoside.

17. The oligomeric compound of or claim 16 wherein said internal region comprises from about 8 to about 14 contiguous β-D-2'-deoxyribofuranosyl nucleosides.

18. The oligomeric compound of claim 16 wherein said internal region comprises from about 9 to about 12 contiguous β-D-2'-deoxyribofuranosyl nucleosides.

19. The oligomeric compound of claim 9 wherein each internucleoside linking group is, independently, a phosphodiester internucleoside linking group or a phosphorothioate internucleoside linking group.

20. The oligomeric compound of claim 9 wherein essentially each internucleoside linking group is a phosphorothioate internucleoside linking group.

21. The oligomeric compound of any one of claim 9 comprising from about 8 to about 40 linked monomer subunits.

22. A method of inhibiting gene expression comprising contacting one or more cells, a tissue or an animal with an oligomeric compound of claim 9.

* * * * *

UNITED STATES PATENT AND TRADEMARK OFFICE
CERTIFICATE OF CORRECTION

PATENT NO.         : 8,536,320 B2                                         Page 1 of 1
APPLICATION NO. : 13/146188
DATED              : September 17, 2013
INVENTOR(S)        : Prakash et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this

Fifteenth Day of September, 2015

Michelle K. Lee
*Director of the United States Patent and Trademark Office*